(12) United States Patent
Adger et al.

(10) Patent No.: US 8,404,843 B2
(45) Date of Patent: Mar. 26, 2013

(54) CHIRAL PHOSPHORUS COMPOUND

(75) Inventors: Brian Adger, Cambridge (GB); Alan Dyke, London (GB); Giancarlo Francio, Aachen (DE); Frederick Ernest Hancock, Hertfordshire (GB); Walter Leitner, Aachen (DE); Thomas Pullmann, Aachen (DE); Andreas Seger, Cambridgeshire (GB); Antonio Zanotti-Gerosa, Cambridge (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 13/531,986

(22) Filed: Jun. 25, 2012

(65) Prior Publication Data

US 2012/0264940 A1  Oct. 18, 2012

Related U.S. Application Data

(62) Division of application No. 12/444,289, filed as application No. PCT/GB2007/050602 on Oct. 1, 2007, now Pat. No. 8,222,415.

(30) Foreign Application Priority Data

Oct. 3, 2006 (GB) .................................. 0619494.8

(51) Int. Cl.
*C07F 9/60* (2006.01)
(52) U.S. Cl. ......................................................... 546/23
(58) Field of Classification Search .................. None
See application file for complete search history.

(56) References Cited

U.S. PATENT DOCUMENTS 6,720,281 B2    4/2004   Leitner et al.

FOREIGN PATENT DOCUMENTS

| CA | 2 278 572 A1 | 7/1998 |
| WO | WO-98/32533 A1 | 7/1998 |

OTHER PUBLICATIONS

Ager et al., "Convenient and direct preparation of tertiary phosphines via nickel-catalysed cross-coupling," *Chem. Commun.*, 1997, pp. 2359-2360.
Allinger et al., "Some Kinetic and Mechanistic Studies of the Dakin-West Reaction," *J. Org. Chem.*, vol. 39, No. 12, 1974, pp. 1730-1735.
Amiot et al., "Enantioselective nucleophilic addition of organometallic reagents to quinoline: regio-, stereo- and enantioselectivity," *Tetrahedron* 60 (2004), pp. 8221-8231.
Baillie et al., "Palladium-catalysed synthesis of biaryl phospines," *Tetrahedron* 60 (2004), pp. 4159-4168.
Bálint et al., "Synthesis, absolute configuration and intermediates of 9-fluoro-6,7-dihydro-5-methyl-1-oxo-1*H*,5*H*-benzo[*i,j*]quinolizine-2-carboxylic acid (flumequine)," *Tetrahedron: Asymmetry* 10 (1999), pp. 1079-1087.

Beletskaya et al., "Hydroborations Catalysed by Transition Metal Complexes," *Tetrahedron* 1997, vol. 53, No. 14, pp. 4957-5026.
Botteghi et al., "The Asymmetric Hydroformylation in the Synthesis of Pharmaceuticals," *Chirality* 1991, 3, pp. 355-369.
Burk et al., "Ruthenium-catalysed asymmetric hydrogenation of ketones using QUINAPHOS as the ligand," *Chem. Commun.*, 2005, pp. 3460-3462.
Cai et al., "Synthesis of Chiral 2,2'-Bis(diphenylphosphino)-1,1'-binaphthyl (BINAP) via a Novel Nickel-Catalyzed Phosphine Insertion," *J. Org. Chem.* 1994, 59, pp. 7180-7181.
Cointeaux et al., "Enantioselective addition of organolithium reagents to quinoline catalyzed by 1,2-diamines," *Tetrahedron: Asymmetry* 16 (2005), pp. 925-929.
Cui et al., "Catalytic Homogeneous Asymmetric Hydrogenations of Largely Unfunctionalized Alkenes," *Chem. Rev.* 2005, 105, pp. 3272-3296.
Davies et al., "Asymmetric Synthesis of (+)-Negamycin," *Tetrahedron: Asymmetry* 1996, vol. 7, No. 7, pp. 1919-1922.
Denmark et al., "On the Mechanism of the Skraup-Doebner-Von Miller Quinoline Synthesis," *J. Org. Chem.* 2006, 71, pp. 1668-1676.
Franciò et al., "Asymmetric Catalysis with Chiral Phosphane/Phosphoramidite Ligands Derived from Quinoline (QUINAPHOS)," *Angew. Chem. Int. Ed.* 2000, 39, No. 8, pp. 1428-1430.
Herrmann et al., "Water-Soluble Ligands, Metal Complexes, and Catalysts: Synergism of Homogeneous and Heterogeneous Catalysis," *Angew. Chem. Int. Ed. Engl.*, 1993, vol. 32, pp. 1524-1544.
Ikariya et al., "Bifunctional transition metal-based molecular catalysts for asymmetric syntheses," *Org. Biomol. Chem.*, 2006, 4, pp. 393-406.

(Continued)

*Primary Examiner* — Janet Andres
*Assistant Examiner* — Timothy R Rozof
(74) *Attorney, Agent, or Firm* — RatnerPrestia

(57) ABSTRACT

The present invention relates to novel chiral phosphorus compounds which can be readily prepared from quinoline derivatives as inexpensive starting compounds and have the general formula (I)

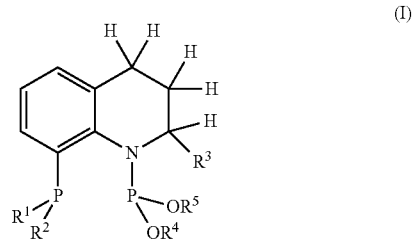

(I)

wherein $R^1$, $R^2$, $R^3$, $R^4$, $R^5$ are chiral or achiral organic residues which are derived from substituted or unsubstituted straight or branched chain or cyclic aliphatic or aromatic groups and which, in the case of the pairs $R^1/R^2$ and $R^4/R^5$, may be interconnected. Further, the invention relates to methods for the synthesis of chiral phosphorus compounds of general formula (I) and their use as catalyst components in processes for the preparation of optically active products.

8 Claims, No Drawings

OTHER PUBLICATIONS

Ma et al., "Mild Method for Ullmann Coupling Reaction of Amines and Aryl Halides," *Organic Letters* 2003, vol. 5, No. 14, pp. 2453-2455.

Ma et al., CuI-Catalyzed Coupling Reaction of β-Amino Acids or Esters with Aryl Halides at Temperature Lower Than That Employed in the Normal Ullmann Reaction. Facile Syntheis of SB-214857, *Organic Letters* 2001, vol. 3, No. 16, pp. 2583-2586.

Nagel et al., "The enantioselective hydrogenation of N-Acyl dehydroamino acids," *Topics in Catalysis* 1998, 5, pp. 3-23.

Noyori et al., "Asymmetric Catalysis by Architectural and Functional Molecular Engineering: Practical Chemo- and Stereoselective Hydrogenation of Ketones," *Angew. Chem. Int. Ed.* 2001, 40, pp. 41-73.

Qiu et al., "A New Class of Versatile Chiral-Bridged Atropisomeric Diphosphine Ligands: Remarkably Efficient Ligand Syntheses and Their Applications in Highly Enantioselective Hydrogenation Reactions," *J. Am. Chem. Soc.* 2005, 128, pp. 5955-5965.

Rueping et al., "A Highly Enantioselective Brønsted Acid Catalyzed Cascade Reaction: Organocatalytic Transfer Hydrogenation of Quinolines and their Application in the Synthesis of Alkaloids," *Angew. Chem. Int. Ed.* 2006, 45, pp. 3683-3686.

Shuttleworth et al., "Functionalised Polymers: Recent Developments and New Applications in Synthetic Organic Chemistry." *Synthesis* 1997 (11), pp. 1217-1239.

Stadler et al., "Rapid Formation of Triarylphosphines by Microwave-Assisted Transition Metal-Catalyzed C-P Cross-Coupling Reactions," *Organic Letters* 2002, vol. 4, No. 20, pp. 3541-3543.

Gelman et al., "Copper-Catalyzed C-P Bond Construction via Direct Coupling of Secondary Phosphines and Phosphites with Aryl and Vinyl Halides," *Organic Letters* 2003, vol. 5, No. 13, pp. 2315-2318.

Hartwig et al., "Room-Temerature Palladium-Catalyzed Aminations of Aryl Bromides and Chlorides and Extended Scope of Aromatic C-N Bond Formation with a Commercial Ligand," *J. Org. Chem.* 1999, 64, pp. 5575-5580.

Taguchi et al., "Synthesis of quinolines from amino alcohol and ketones catalyzed by [IrCL(cod)]$_2$ or IrCl$_3$ under solvent-free conditions," *Tetrahedron Letters* 46 (2005), pp. 4539-4542.

Theeraladanon et al., "Total synthesis of (+)-(S)-angustureine and the determination of the absolute configuration of the natural product angustureine," *Tetrahedron: Asymmetry* 16 (2005), pp. 827-831.

Van Allen et al., "Copper-Catalyzed Synthesis of Unsymmetrical Triarylphosphines," *J. Org. Chem.* 2003, 68, pp. 4590-4593.

Wang et al., "Highly Enantioselective Iridium-Catalyzed Hydrogenation of Heteroaromatic Compounds, Quinolines," *J. Am. Chem. Soc.* 2003, 125, pp. 10536-10537.

Wehman et at., "Influence of various P/N and P/P ligands on the palladium-catalysed reductive carbonylation of nitrobenzene," *Journal of Organometallic Chemistry* 535 (1997), pp. 183-193.

Wolfe et al., "Simple, Efficient Catalyst System for the Palladium-Catalyzed Amination of Aryl Chlorides, Bromides and Triflates," *J. Org. Chem.* 2000, 65, pp. 1158-1174.

Wolfe et al., "Scope and Limitations of the Pd/BINAP-Catalyzed Amination of Aryl Bromides," *J. Org. Chem.* 2000, 65, pp. 1144-1157.

Yamaguchi, "Regio- and Stereoselective α-allylation of quinolines activated by chloroformate and triflate ion by means of chiral allylsilane: a synthesis of chiral 2-substituted 1,2-dihydroquinolines," *Tetrahedron Letters* 2002, 43, pp. 8871-8874.

Allen et al., "Resolutions Involving Metal Complexation. Preparation and Resolution of (R,S)-Methylphenyl(8-quinolyl)phosphine and Its Arsenic Analogue. Crystal and Molecular Structure of (+)$_{589}$-[(R)-Dimethyl(1-ethyl-α-naphthyl)aminato-$C^2$,N]-[(S)-methylphenyl(8-quinolyl)phosphine]palladium(II) Hexafluorophosphate," *Inorg. Chem.* 1982, 21, pp. 1007-1014.

*The Catalyst Technical Handbook*, © 2005 Johnson Mathey PLC, pp. 1, 2, 27-29, 63-66, 69-71, and 73-85.

CHIRAL PHOSPHORUS COMPOUND

CROSS-REFERENCE TO RELATED APPLICATIONS

This application is a divisional application of U.S. patent application Ser. No. 12/444,289, filed Jun. 4, 2010, which is a U.S. National Phase application of PCT/GB2007/050602, filed Oct. 1, 2007, and claims priority of British Patent Application No. 0619494.8, filed Oct. 3, 2006, the disclosures of all of which are incorporated herein by reference in their entireties for all purposes.

FIELD OF THE INVENTION

The present invention relates to novel chiral phosphorus compounds that can be readily prepared from quinoline derivatives, and their use as catalysts or catalyst components in processes for the preparation of optically active products.

BACKGROUND OF THE INVENTION

Chiral phosphorus compounds are of great interest as catalysts or catalyst components ("ligands") for the enantioselective chemical synthesis of optically active products (*Handbook of Enantioselective Catalysis with Transition Metal Compounds*, Vol. II, VCH, Weinheim, 1993). Optically active products are of great economic importance as flavouring agents, cosmetics, plant protectants, food additives, pharmaceuticals, or in the preparation of high-tech materials, such as special plastics (*Comprehensive Asymmetric Catalysis*, Springer, Berlin, 1999). To date, despite of the wide variety of known chiral phosphorus compounds, only a few members have been put to use in industrial processes for the preparation of optically active products, because many ligands have serious disadvantages for technical applications. Many ligands, although exhibiting high enantioselectivities, form the desired chiral products with too low activities or insufficient chemo- or regioselectivities. Further, chiral phosphorus compounds which act as efficient ligands are often available only by tedious syntheses using expensive starting materials. In most efficient ligands, the chiral information which results in the selective formation of the optically active products is based on the use of chiral building blocks which are either derived from naturally occurring compounds or otherwise commercially available in an optically pure form. A structural variation in the chiral centre for optimising the phosphorus compound cannot be realized in a simple way in this case, and often only one of the two possible configurations is available. Therefore, there is a great need for novel chiral phosphorus compounds which can be synthesized in a simple and flexible way from readily available and inexpensive starting compounds and can be effectively employed as catalysts or catalyst components for the preparation of chiral products in various types of reaction.

U.S. Pat. No. 6,720,281 describes novel phosphorus compounds derived from quinoline derivatives. These ligands are effective in many circumstances, however the remains a need to provide alternative quinoline-based compounds that may be used in asymmetric catalysts.

SUMMARY OF THE INVENTION

The present invention relates to a novel class of chiral phosphorus compounds of general formula (I)

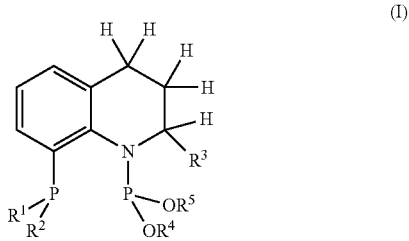

wherein $R^1$, $R^2$, $R^3$, $R^4$, $R^5$ are chiral or achiral organic residues which are derived from substituted or unsubstituted straight or branched chain or cyclic aliphatic or aromatic groups and which, in the case of the pairs $R^1/R^2$ and $R^4/R^5$, may be interconnected. These compounds can be prepared simply and in few steps from derivatives of quinoline as inexpensive starting materials. The chiral information in the 2-position of the quinoline skeleton, which is critical to the selective formation of the desired optically active products, is produced during the synthesis and can be easily varied by selecting $R^3$. The two isomers with the different configurations in the 2-position can be effectively separated from each other. The compounds of formula (I) can be employed as efficient catalysts or catalyst components in the preparation of optically active products, wherein high activities and selectivities are achieved especially in enantioselective hydroformylation and hydrogenation.

DETAILED DESCRIPTION OF THE INVENTION

The synthesis of compound (I) can be accomplished by a variety of synthetic approaches. In one embodiment, the synthesis of compounds (I) may proceed via the "Quinaphos" compounds (VI). Synthesis of the "Quinaphos" compounds (VI) may conveniently start from 8-phosphinoquinolines (II) as follows; (see Scheme 1).

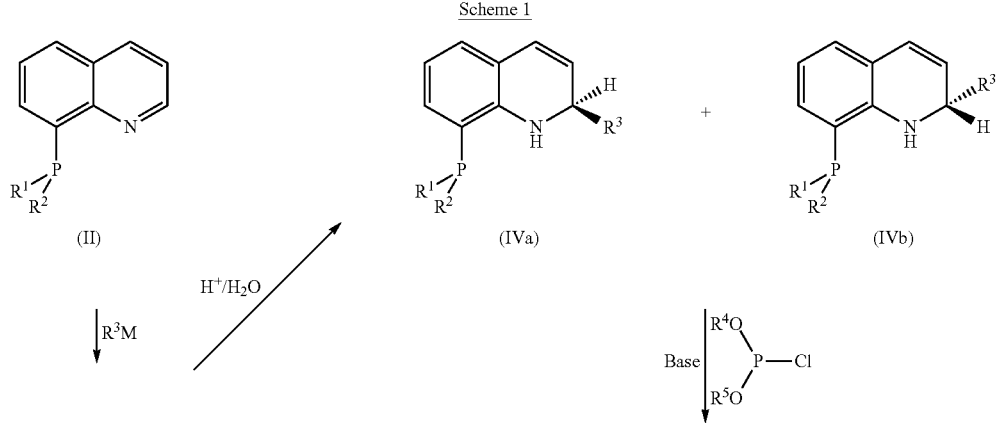

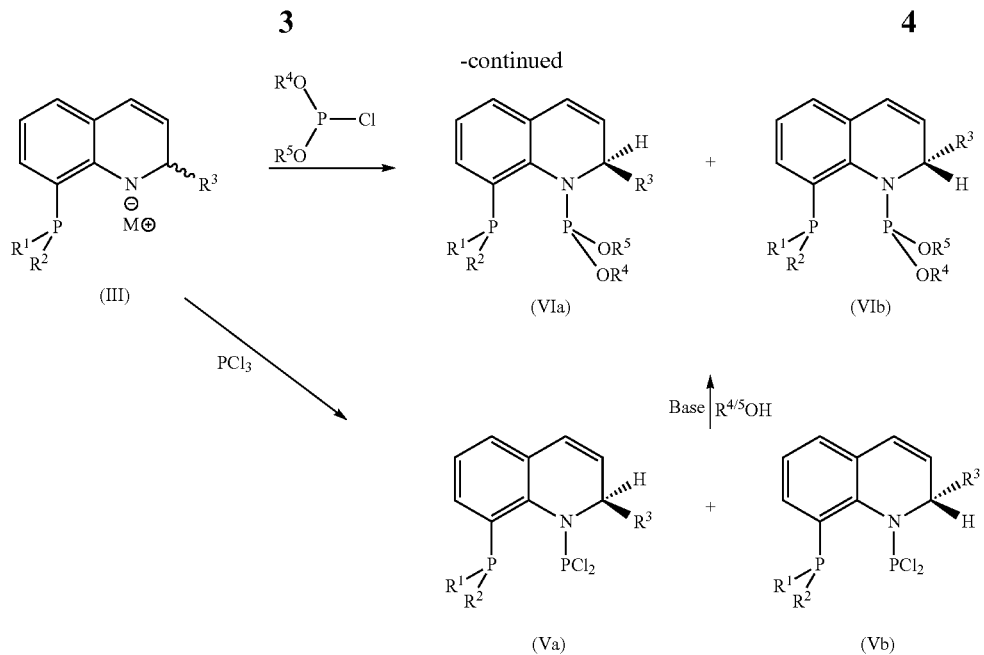

It will be understood that, in the depictions herein, where $R^3$ is connected by a curly line (~) both enantiomers may be present. Compounds (II) are already known and different residues $R^1$ and $R^2$ and can be easily prepared on a multigram scale via different routes (typical examples: *Inorg. Chem.* 1982, 21, 1007; *J. Organomet. Chem.* 1997, 535, 183). By means of these syntheses and suitable simple modifications, compounds of formula (II) can be prepared in which $R^1$ or $R^2$ are the same or different chiral or achiral organic residues which are derived from substituted or unsubstituted straight or branched chain or cyclic aliphatic or aromatic groups and may be interconnected. Residues $R^1$ and $R^2$ can be independently selected from the groups methyl, ethyl, n-propyl, i-propyl, n-butyl, t-butyl, hexyl, $F(CF_2)_m(CH_2)_n$— (m=1-10, n=0-4), cyclo-hexyl, menthyl, allyl, benzyl, $CH_3O(CH_2)_2OCH_2$—, phenyl, tolyl, anisyl, trifluoro-methylphenyl, $F(CF_2)_m(CH_2)_nC_6H_4$— (m=1-10, n=0-4), bis(trifluoromethyl)phenyl, chlorophenyl, pentafluorophenyl, hydroxyphenyl, carboxyphenyl, $NaO_3SC_6H_4$—, naphthyl, fluorenyl, pyridyl or furyl, the groups mentioned not being intended to imply any limitation to the scope of application. When the two groups are interconnected, there may be formed substituted or unsubstituted chiral or achiral bridges which are derived, for example, from the skeletons —$(CH_2)_n$— (n=2-4), —CH($CH_3$)CH($CH_3$)—, —CH($CH_3$)$CH_2$ CH($CH_3$)—, 1,1'-binaphth-2,2'-diyl, again no limitation being implied by this listing.

The reaction of compound (II) with nucleophilic reagents $R^3M$ yields compounds (III), wherein $R^3$ refers to the same definition as $R^1$ or $R^2$. The addition in 2-position of the quinoline can be accomplished with Grignard compounds (M=MgHal, Hal=halogen) and many other organometallic compounds (e.g., M=Li, ZnR, $SnR_3$, $SiR_3$; R=alkyl or aryl residue), so that a wide variety of possible derivatives results. The addition in 2-position of the quinoline produces a chiral centre, the stereochemistry at this centre not being defined in the absence of an additional chiral auxiliary or catalyst. In the presence of a chiral auxiliary or catalyst, the addition of $R^3M$ may performed in an enantioselective manner (e.g. see F. Amiot, L. Cointeaux, E. J. Silve, A. Alexakis *Tetrahedron* 2004, 60, 8221-8231; L. Cointeaux, A. Alexakis *Tetrahedron: Asymmetry* 2005, 16, 925-929). Enantioselective addition may be achieved also using chiral reagents (see e.g. R. Yamaguchi, M. Tanaka, T. Matsuda, T. Okano, T. Nagura, K. Fujita *Tetrahedron Letters* 2002, 43, 8871-8874).

Compounds (III) may be converted to the 1,2-dihydroquinoline derivatives (IV) by hydrolysis using e.g. water or aqueous acid. Reaction with chlorophosphinites $(R^4O)(R^5O)$PCl in the presence of bases such as triethylamine or pyridine yields the desired phosphorus compounds of formula (VI). An alternative approach depicted above is the reaction of compound (III) with $PCl_3$ to form the dichlorophosphine derivatives (V). A further approach, not depicted, is the reaction of compound (III) with $P(NEt_2)_2Cl$ or $P(NMe_2)_2Cl$ to form the bis(di-ethylamino)phosphine or bis(di-methylamino)phosphine derivatives, respectively, which upon reaction with alcohols or diols again yields compounds (VI). Compounds (III) can also be reacted directly with chlorophosphinites $(R^4O)(R^5O)PCl$ without further addition of bases to (VI).

The residues $R^4$ and $R^5$ may be the same or different, achiral or chiral, and may be interconnected. Otherwise, the residues have the same definition as residues $R^1$ and $R^2$. Examples of alcohols and diols which may be used for the preparation of the corresponding compounds $(R^4O)(R^5O)$ PCl or directly reacted with compounds (V) include methanol, ethanol, iso-propanol, benzyl alcohol, cyclohexanol, allyl alcohol, phenol, methylphenol, chlorophenol, naphthol, furfurol, ethylene glycol, 1,3-propanediol, 1,3-pentanediol, cyclohexanediol, glycerol, monosaccharides, oligosaccharides, catechol, 2,2'-dihydroxy-1,1'-biphenyl, 3,3',5,5'-tetratert-butyl-2,2'-dihydroxy-1,1'-biphenyl, 3,3'-di-tert-butyl-2,2'-dihydroxy-5,5'-dimethoxy-1,1'-biphenyl, 5,5'-dichloro-4,4',6,6'-tetramethyl-2,2'-dihydroxy-1,1'-biphenyl or 2,2'-dihydroxy-1,1'-binaphthyl, the listing not being intended to imply any limitation to the scope of application.

When optically active $(R^4O)(R^5O)P$ groups are used, compounds (VI) are obtained as diastereomers which can be separated by crystallization, chromatography or other suitable separation methods. Alternatively, the separation of the two stereoisomers can be effected on the stage of the 1,2-dihydroquinoline derivatives (IV), which can be resolved by conventional methods into enantiomers (IVa) and (IVb) (see, for example, *Tetrahedron Asymmetry* 1999, 10, 1079).

In one embodiment, synthesis of (I) may be by hydrogenation of a 1,2-dihydroquinoline ring (see Scheme 2).

Scheme 2

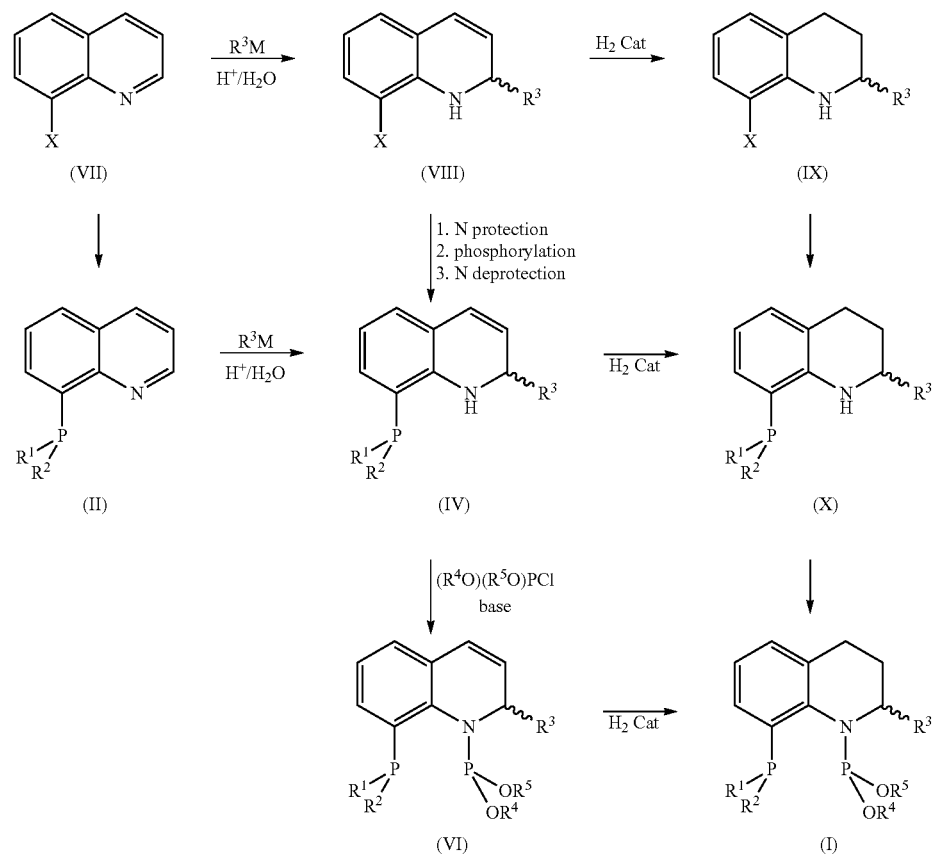

Hence compounds of formula (I) may be prepared from the "Quinaphos" compounds (VI) by selective hydrogenation of the double bond in the dihydroquinoline ring in the presence of known heterogeneous hydrogenation catalysts, e.g. palladium, platinum, rhodium, ruthenium, iridium supported on carbon, alumina, silica etc. Suitable catalysts are described in the *Johnson Matthey Technical Handbook* 2005. Alternatively hydrogenation may be accomplished using homogeneous hydrogenation catalysts that are known to reduce carbon-carbon double bonds, such as iridium complexes bearing phosphine-oxazoline ligands, Crabtree catalyst, rhodium complexes bearing ferrocenyl and paracylophane-based diphosphines etc. Suitable catalysts are described in X. Cui, K. Burgess *Chem. Rev.* 2005, 105, 3272. Heterogeneous catalysts of palladium may be particularly suited to achieve the desired transformation. All above-mentioned hydrogenation procedures may require the protection of the phosphine and phosphoramidite groups e.g. as the corresponding $BH_3$-derivatives. Compounds (I) are then obtained after removal of the $BH_3$ protecting groups e.g. with an amine.

Alternatively, the selective hydrogenation of the carbon-carbon double bond of the dihydroquinoline ring may be applied to intermediate compound (IV). The resulting compound (X) may be easily transformed into compound (I) by the same procedure used to prepare "Quinaphos" compound (VI).

Accordingly the invention further provides the intermediate chiral phosphorus compound of formula (X):

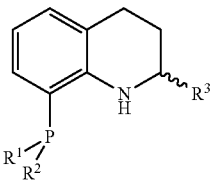

(X)

wherein $R^1$, $R^2$, $R^3$ are chiral or achiral groups selected from the list consisting of substituted or unsubstituted straight-chain, branched-chain or cyclic aliphatic or aromatic groups and in which the pair $R^1/R^2$ may be interconnected to form a ring.

The selective hydrogenation of the carbon-carbon double bond of the 1,2-dihydroquinoline ring can also be performed on intermediates (VIII), prepared from starting material (VII), bearing in position 8 of the dihydroquinoline ring a group X that is a precursor of the phosphine substituent (such as bromide, chloride, iodide, hydroxy, alkoxy, trifloromethylsulphonyloxy etc). Compounds (VII) are readily available or may be synthesized from quinoline using known methods. The transformation of compounds (VIII) and (IX) into compounds (IV) and (X) respectively, may require the protection of the secondary amine by standard methods before the phosphine group $R^1R^2P—$ is introduced in position 8 via a sequence of lithiation and reaction with the appropriate chloro-phosphine electrophyle or via coupling with an appropriate phosphorus containing compound in the presence of a transition metal catalyst. For example, Pd or Ni-catalysed coupling with secondary phosphines is described in A. Stadler, C. O. Kappe *Org. Lett* 2002, 4, 3541; D. Cai et al. *J. Org. Chem.* 1994, 59, 7180; J. Xiao et al. *Tetrahedron* 2004, 60, 4159; copper catalysed coupling with secondary phosphines and phosphates is described in D. Gelman, L. Jiang, S. L. Buchwald: *Org. Lett.* 2003, 5, 2315; D. Van Allen, D. Venkataraman *J. Org. Chem.* 2003, 68, 4590; and nickel catalysed coupling with chlorophosphines is described in S. Lanemann et al. *Chem. Commun.* 1997, 2359; and references therein.

The selective hydrogenation of the carbon-carbon double bond of the 1,2-dihydroquinoline ring does not affect the obtainment of enantiomerically enriched compound (Ia) and (Ib) since the resolution of racemic (I) can be achieved at any stage of the synthetic pathways here described. The residue $R^3$, in this route, may be introduced by nucleophilic addition to the quinoline ring as previously disclosed in the aforesaid U.S. Pat. No. 6,720,281.

In an alternative embodiment, synthesis of the compound of formula (I) may be by asymmetric hydrogenation of the quinoline ring (see Scheme 3). Hence quinolines (XII) can be selectively hydrogenated in the presence of homogeneous transition metal, particularly iridium, hydrogenation catalysts bearing one or more chiral ligands, such as diphosphine or phosphorus-nitrogen ligands, and iodine to produce enantiomerically enriched intermediates (Xa) or (Xb). A suitable method is disclosed by W-B. Wang, S-M. Lu, P-Y. Yang, X-W. Han, Y-G. Zhou *J. Am. Chem. Soc.* 2003, 125, 10536 and W. H. Lam, S. Chan, W.-Y. Yu, Y.-M. Li, R. Guo, Z. Zhou, A. S. C. Chan *J. Am. Chem. Soc.* 2006, 128, 5955-5965.

It is possible that the phosphine group in position 8 of the quinoline may interact with the homogeneous transition metal catalyst and that this interaction may, in some cases, inhibit the hydrogenation. To avoid this problem the asymmetric hydrogenation may be performed on intermediates (XI) bearing in position 8 of the dihydroquinoline ring a group X that is a precursor of the phosphine substituents (such as bromide, chloride, iodide, hydroxy, alkoxy, trifloromethylsulphonyloxy etc). The resulting compounds (IXa) and (IXb) may be transformed into compound (I) by via known synthetic transformations. Alternatively, the interference of phosphine group in the intermediate (XII) during the hydrogenation may be avoided by transforming it into the corresponding oxide or protecting it as $BH_3$-adduct. After partial hydrogenation of the quinoline ring, reduction of the phosphine oxide group back to phosphine group using known procedures (e.g. with trichlorosilane) or treatment of the $BH_3$-adduct with an amine, generates compounds (IXa) and (IXb).

In alternative to metal catalysed hydrogenation, enantioselective Brønsted acid catalysed transfer hydrogenation may be also used as reported by M. Rueping, A. P. Antonchick, T. Theissmann *Angew. Chem. Int. Ed.* 2006, 45, 3683-3686.

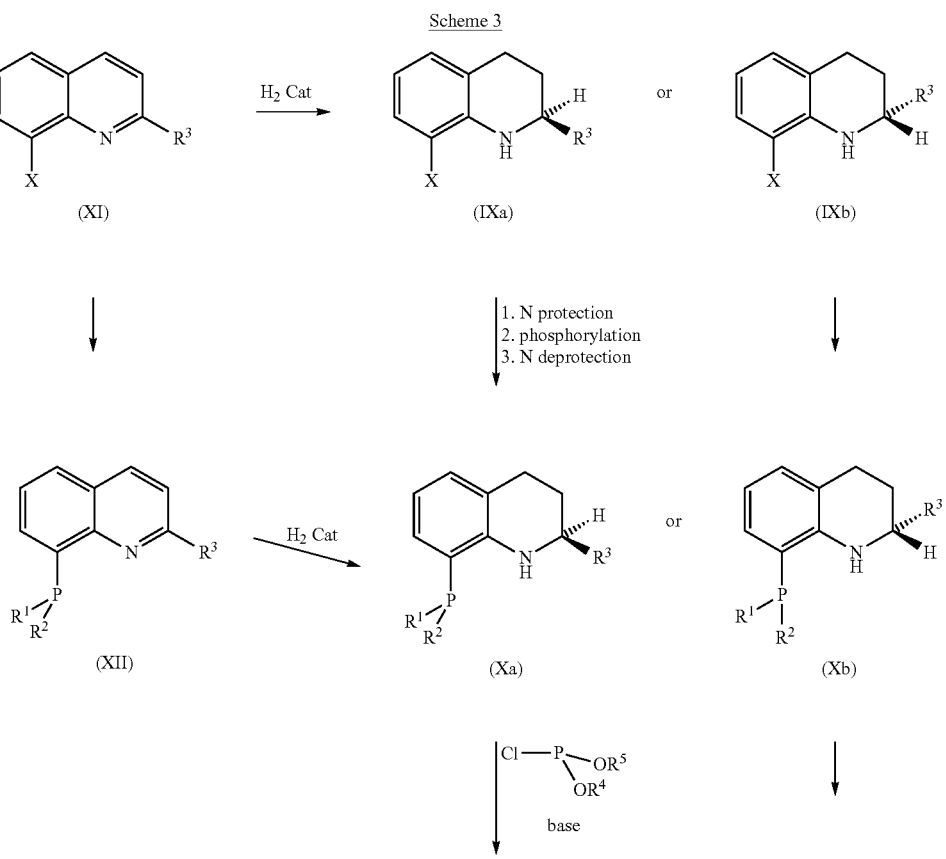

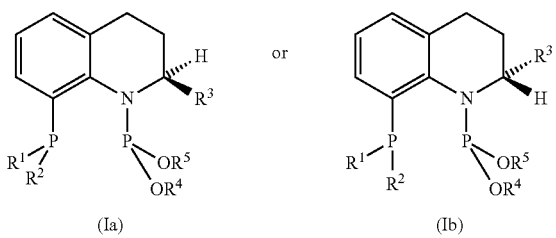

This synthetic approach has the advantage of fixing the stereogenic center in postion 2 without the need of the resolution of racemic (I) or any of the intermediates leading to (I). Another advantage of this route is that the residue $R^3$ is already present in the quinoline ring. Quinolines (XI) substituted in position 2 can be prepared by a variety of methods such as the Skraup-Doebner-Von Miller quinoline synthesis (review: N. L. Allinger, G. L. Wang, B. B. Dewhurst *J. Org. Chem.* 1974, 12, 1730; S. E. Denmark, S. Venkatraman *J.* *Org. Chem.* 2006, 7, 1668) and Friedlander reaction. New efficient iridium and ruthenium catalysed cyclisation reactions to form 2-substituted quinolines have recently been reported in the literature (K. Taguchi, S. Sakaguchi, Y. Ishii *Tetrahedron Letters* 2005, 4539 and references therein).

Compounds (VIII) and (IX) may be synthesised from readily available aniline compounds as follows; (see Scheme 4).

Scheme 4

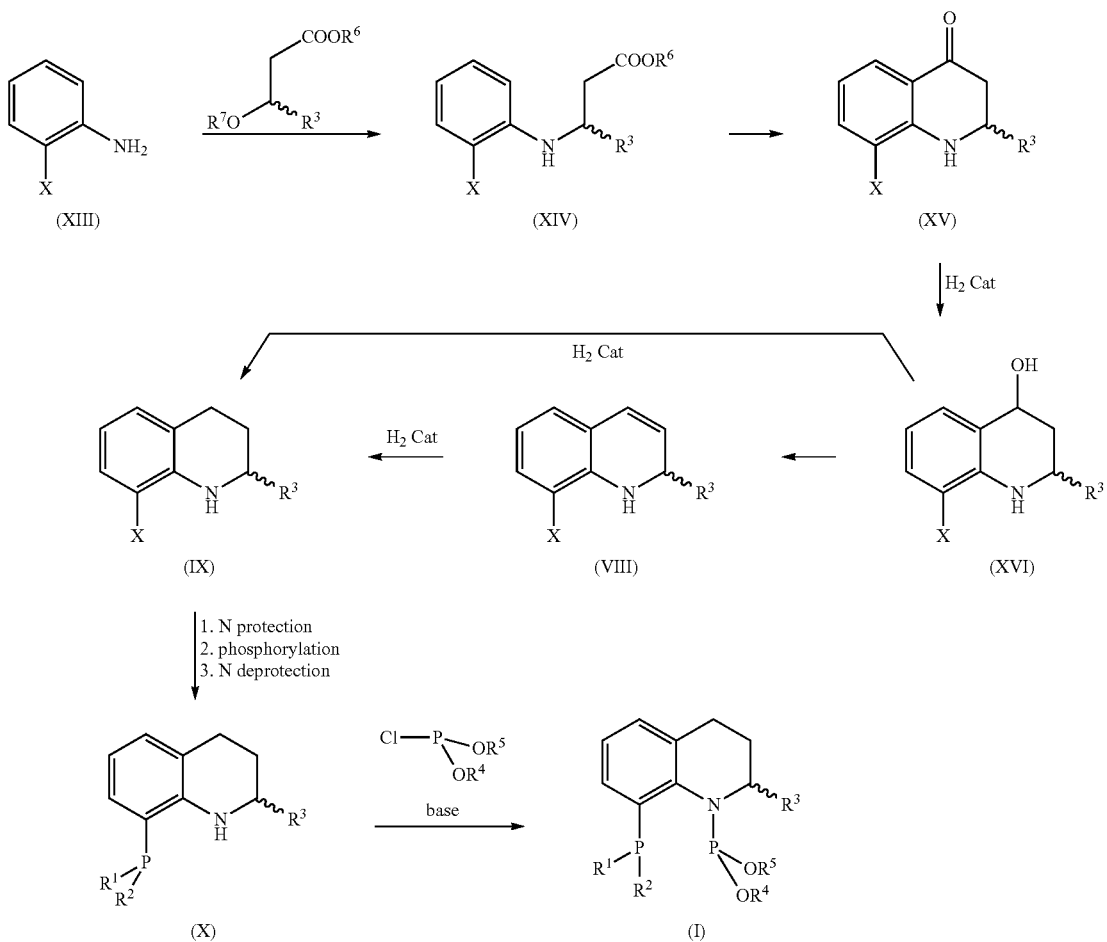

$R^6$ = H, Cl or C1-C10 alkyl
$R^7$ = C1-C10 alkyl, silyl, Ts, Ms, Tf, Ac, H

The acyclic intermediates (XIV) may be readily synthesised from compounds (XIII) using a R³-functional carboxylic acid, ester or chloride of formula R⁷OCHR³CH₂COOR⁶ in which R⁶ may be H, Cl or C1-C10 alkyl (aliphatic, branched or cyclic, including benzyl) and R⁷ may be C1-C10 alkyl (aliphatic, branched or cyclic, including benzyl), Tosyl, Mesyl, Triflate, Acetyl, H or a silyl protecting group such as TMS. The cyclisation to (XV) may be accomplished by standard transformations. Compound (XV) may be reduced to a benzylic alcohol (XVI) that will give intermediates (VIII) and (IX) using steps of elimination/hydrogenation or hydrogenolysis of benzylic alcohol. Aromatic ketones can be hydrogenated to the corresponding alcohols in the presence of a variety of heterogeneous catalysts (for example, palladium on carbon, *Johnson Matthey Technical Handbook* 2005) or homogeneous catalysts (for example, ruthenium or rhodium or iridium complexes) with both hydrogen gas or hydrogen donors such as formic acid, sodium formate etc, (*Johnson Matthey Technical Handbook* 2005, R. Noyori, T. Ohkuma *Angew. Chem. Int. Ed.* 2001, 40, 40; T. Ikariya, K. Murata, R. Noyori *Org. Biomol. Chem.* 2006, 4, 393). Hydrogenolysis in the presence of heterogeneous hydrogenation catalysts is favoured by acid conditions, elevated temperatures and protic solvents and will lead directly to compound (IX) without any need of isolating intermediate (VIII).

Intermediates (VIII) and (IX) may be transformed into compound (I) via known synthetic transformations (for example, as described in J. March *Advanced Organic Chemistry*, Wiley 1992.

Compounds (Ia) and (Ib) can then be obtained in enantiomerically pure form by resolution of any of the intermediates.

Scheme 5 describes an alternative synthesis based on the concept of building the tetrahydroquinoline ring.

Scheme 5

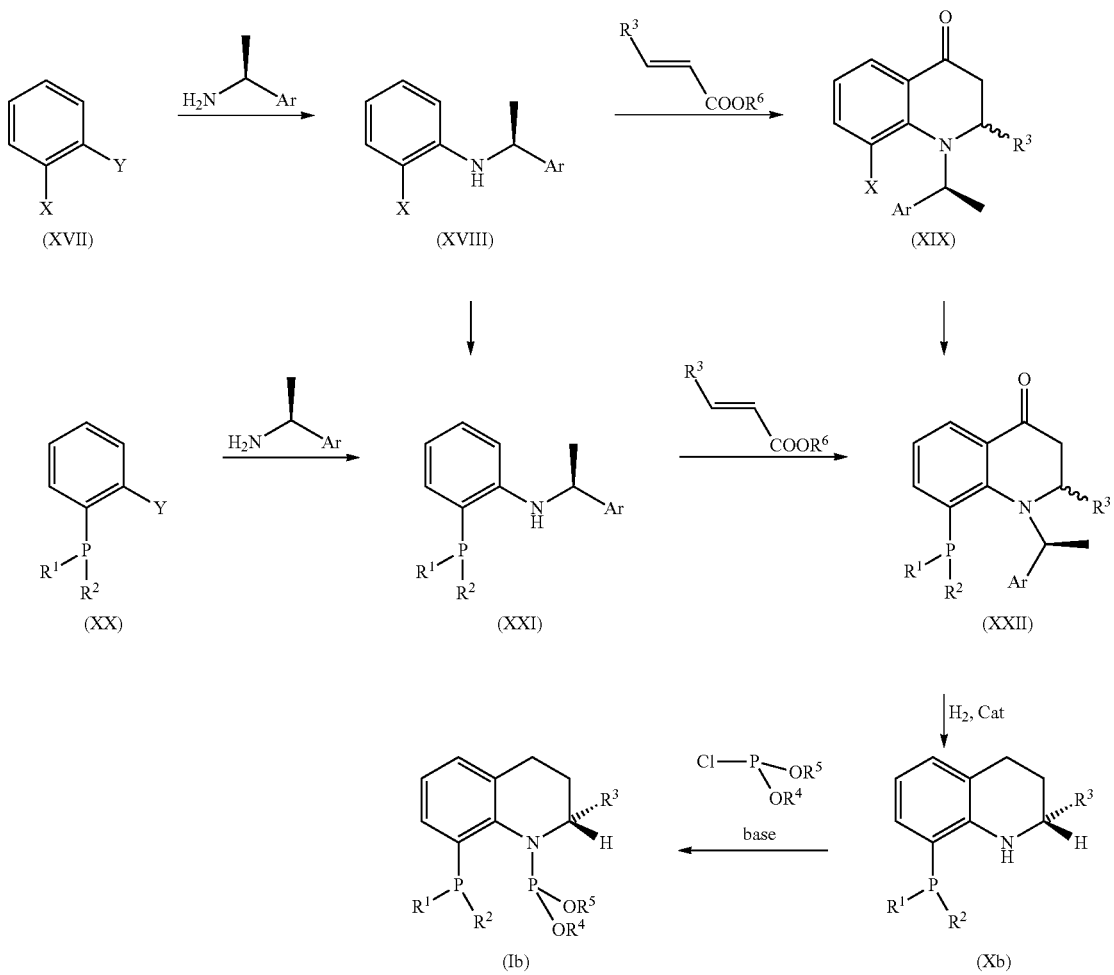

This approach makes use of intermediates (XVIII) or (XXI) where a chiral auxiliary, preferably a chiral amine of formula H₂NCH(CH₃)Ar, in which Ar is an aryl group, such as 2-phenyl-ethylamine, 2-naphtylethylamine has been introduced by coupling on the readily available starting materials (XVII) or (XX). By the term "aryl" we include phenyl, naphthyl and substituted phenyl and naphthyl compounds, such as tolyl or xylyl. In compounds (XVII) and (XX) X may be selected from bromide, chloride, iodide, hydroxy, alkoxy, tosylate, mesylate, nonaflate, fluoride or triflate and Y may be selected from fluoride, chloride, bromide, iodide, tosyl, mesyl, triflate, nonaflate etc. By using Buchwald-Hartwig coupling chemistry (e.g. see J. F. Hartwig et al. *J. Org. Chem.* 1999, 64, 5575; S. L. Buchwald et al. *J. Org. Chem.* 2000, 65, 1158; S. L. Buchwald et al. *J. Org. Chem.* 2000, 65, 1144) enantiomerically pure amines can be coupled with aryl-halides and triflates, tosylates, mesylates etc., without loss of enantiomeric purity. Alternatively, the desired compounds may be obtained via Ulmann coupling (e.g. see D. Ma et al. *Org. Lett.* 2003, 5, 2453).

Compounds (XVIII) or (XXI) may be added to a suitable unsaturated ester with high diatereoselectivity, preferably of formula $R^3CH=CHCOOR^6$, in which $R^6$ is H, Cl or C1-C10 alkyl, preferably C1-C10 alkyl. (This method is described for example in S. G. Davies, O. Ichihara *Tetrahedron: Asymmetry* 1996, 7, 1919). In this case, this procedure may set in place the stereogenic centre in position 2 in high enantiomeric purity Intermediates (XIX) and (XXII) may be transformed into compounds (X) and (I) (here Xb and Ib) via known synthetic transformations. The N-debenzylation may be achieved in one vessel using the same heterogeneous hydrogenation catalysts employed for the reduction of the ketone and hydrogenolysis of derived benzylic alcohol. Alternatively, different catalysts may be employed. Acidic solvents such as acetic acid or buffered solvents are desirable to prevent inhibition of the catalyst.

Alternatively, as described in Scheme 6, starting materials (XVII) or (XX) can be coupled with enantiomerically pure β-aminoesters. (A suitable method is described in D. Ma, C. Xia *Org. Lett.* 2001, 3, 2583).

synthons such as 3-aminoesters and acids, preferably of formula $H_2NCHR^3CH_2COOR^6$ in which $R^6$ may be H or C1-C10 alkyl. The resulting enantiomerically pure compounds (XIVa), (XIVb), (XXIIIa) and (XXIIIb) may be cyclised and reduced to the dehydroquinoline following known chemical transformations.

Enantiomerically pure intermediates (X) or (IX) can be synthesised starting from (XXIV) or (XXVII) as shown in Scheme 7 (for (IXb) and (Xb)) and then further converted to (I) as described in Scheme 3. The reaction sequence is based on a report of C. Theeraladanon, M. Arisawa, M. Nakagawa, A. Nishida *Tetrahedron: Asymmetry* 2005, 16, 827-831. This includes a Mitsunobu coupling of (XXIV) or (XXVII) with readily available enantiomerically pure allylic alcohols to form compounds (XXV) and (XXVIII), respectively, followed by a ring closing metathesis (RCM) to yield (XXVI) and (XXIX), respectively. Reduction of the C=C double bond (described in Scheme 2) and cleavage of the tosyl group gives access to (IX) and (X) from (XXVI) and (XXIX), respectively. In some cases, could be more convenient to perform the last two steps in inverted order, i.e. before the cleavage of the tosyl group and then reduction of the C=C double bond. Compounds (IX) may be phosphorylated as Scheme 6

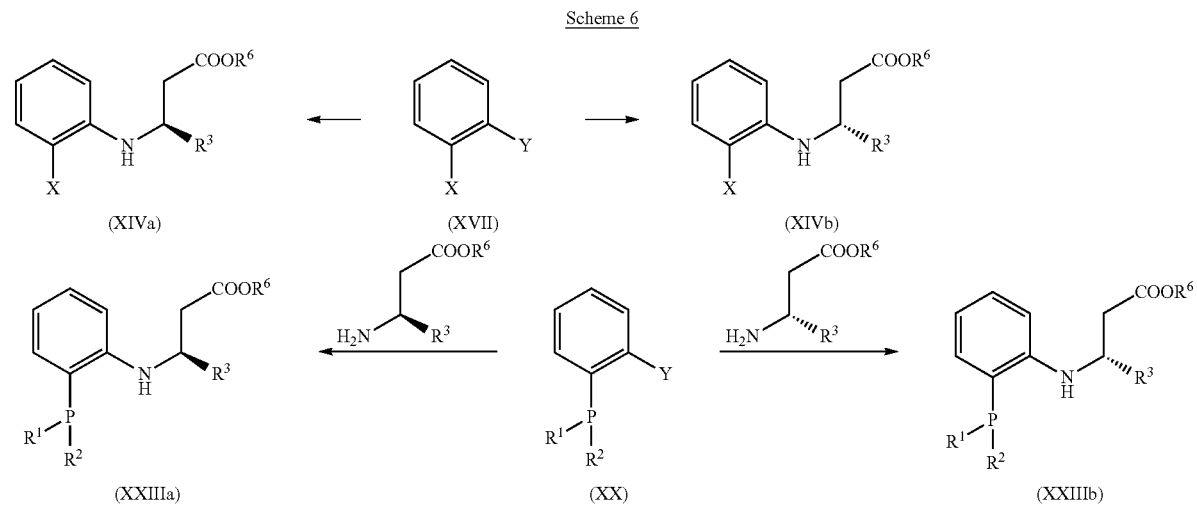

In this case, the desired stereochemistry of position 2 is obtained by the use of readily available enantiomerically pure shown in Scheme 3 or alternatively, compounds (XXVI) may be phosphorylated to form compounds (XXIX).

Scheme 7

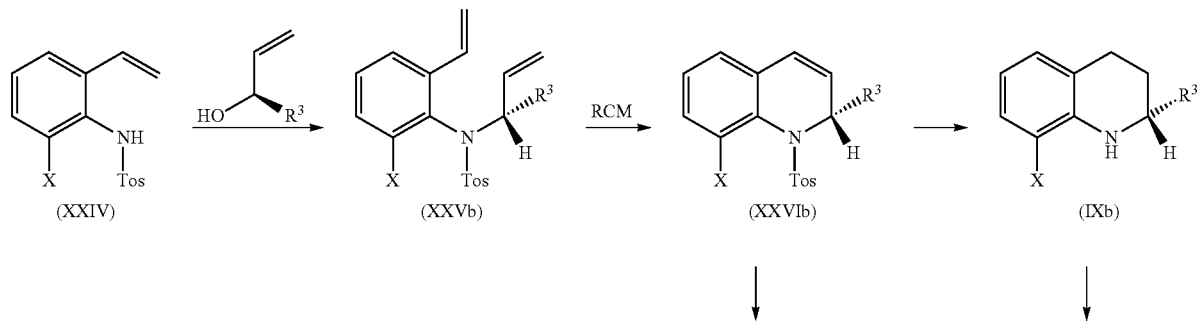

-continued

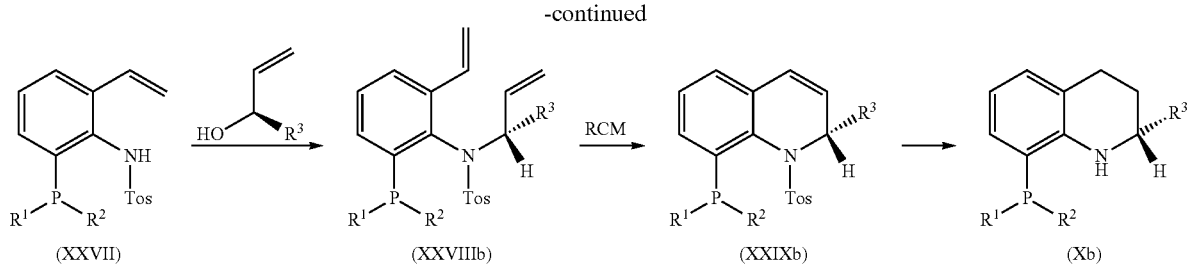

Accordingly, the invention further provides a method for preparing a compound of formula (I) as defined herein, comprising the step of selectively hydrogenating a compound of formula (VI) to hydrogenate the carbon-carbon double bond in the dihydroquinoline ring.

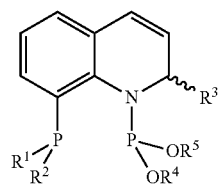

(VI)

The invention further provides a method for preparing a compound of formula (I) as defined herein, comprising the step of reacting a compound of formula (X) with $(R^5O)(R^4O)PCl$.

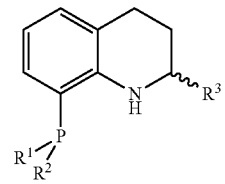

(X)

Compound (X) may be prepared by selectively hydrogenating a compound of formula (IV) to hydrogenate the carbon-carbon double bond in the 1,2-dihydroquinoline ring

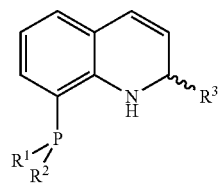

(IV)

Alternatively, compound (X) may be prepared by selectively hydrogenating a compound of formula (VIII), in which X is a group selected from bromide, chloride, iodide, hydroxy, alkoxy, mesylate, tosylate, nonaflate or triflate, to hydrogenate the carbon-carbon double bond in the dihydroquinoline ring to form a compound of formula (IX) and phosphorylating the compound of formula (IX) with a phosphorylating compound.

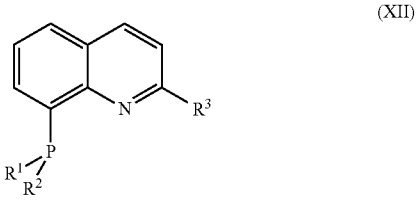

(VIII)

(IX)

By "phosphorylating compound" we mean those phosphorus compounds able to displace X with the $R^1R^2P$— moiety.

Alternatively compound (X) may be made in enantiomerically enriched form by asymmetrically hydrogenating a compound of formula (XII) in the presence of a homogeneous transition metal hydrogenation catalyst having one or more chiral ligand to produce enantiomerically enriched intermediates of formula (Xa) or (Xb).

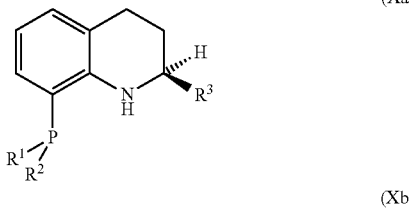

(XII)

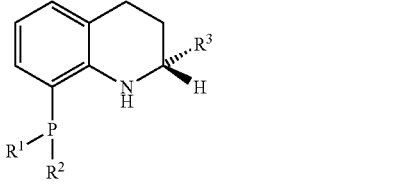

(Xa)

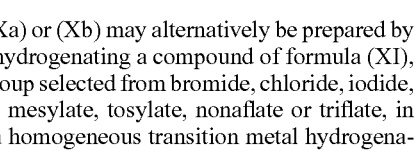

(Xb)

Compounds (Xa) or (Xb) may alternatively be prepared by asymmetrically hydrogenating a compound of formula (XI), in which X is a group selected from bromide, chloride, iodide, hydroxy, alkoxy, mesylate, tosylate, nonaflate or triflate, in the presence of a homogeneous transition metal hydrogenation catalyst having one or more chiral ligand to produce enantiomerically enriched intermediates (IXa or IXb), and reacting intermediates (IXa) or (IXb) with a phosphorylating compound.

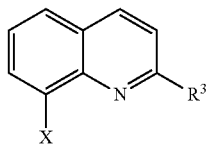
(XI)

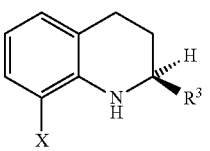
(IXa)

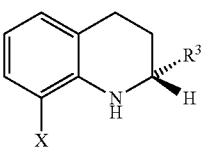
(IXb)

Compounds (Xa) or (Xb) may alternatively be prepared by hydrogenating a ketone compound of formula (XXII).

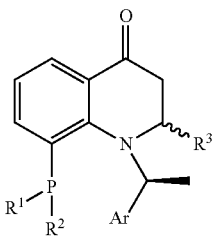
(XXII)

Compounds (Xa) or (Xb) may alternatively be prepared by;

(i) performing a ring closing metathesis on compounds of formula (XXVb) or (XXVa) to form compounds (XXVIb) or (XXVIa), respectively, (ii) cleaving the tosyl group to form compounds (VIIIb) or (VIIIa) respectively, (iii) hydrogenating compounds (VIIIb) or (VIIIa) to form compounds (IXb) or (IXa) respectively, and (iv) phosphorylating compounds (IXb) or (IXa) with a phosphorylating compound to form compounds (Xb) or (Xa), respectively. Steps ii, iii and iv may be performed in different order.

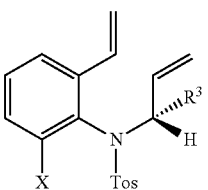
(XXVb)

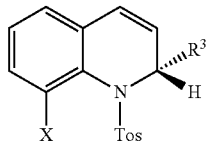
(XXVIb)

Compounds (Xa) or (Xb) may alternatively be prepared by;
(i) performing a ring closing metathesis of compounds of formula (XXVIIIb) or (XXVIIIa) to form compounds (XXIXb) or (XXIXa), respectively,
(ii) cleaving the tosyl group to form compounds (IVb) or (IVa), respectively, and
(iii) hydrogenating compounds (IVb) or (IVa), to form compounds (Xb) or (Xa), respectively. Steps ii and iii may be performed in reverse order.

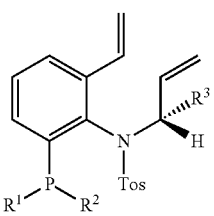
(XXVIIIb)

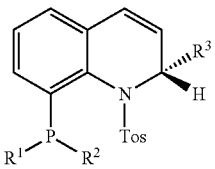
(XXIXb)

The chiral phosphorus compounds (I) can be used in an optically pure form, as a mixture of diastereomers or in the form of the pure diastereomers as effective catalysts or catalyst components in the synthesis of optically active products. Particularly preferred are syntheses in which compounds of formula (I) are employed as components ("ligands") of transition metal catalysts. Such catalysts contain one or more transition metal centres which may be the same or different. Preferred metals include Cu, Ag, Au, Ni, Pd, Pt, Co, Rh, Ir, Fe, Ru, Os, Mn, Re, Cr, Mo, W, Ti or Zr. Particularly preferred are Cu, Ni, Pd, Pt, Rh, Ir or Ru.

The catalysts may be employed in the form of isolated compounds which already contain the metal and the ligand (I), or may be formed in situ from ligand (I) and suitable metal-containing components. As the metal-containing components, the metals themselves, simple salts or complex compounds of the corresponding metals can be used. The molar ratio between the ligand (I) and the metal centre can be optimally adapted for the respective reaction and is usually between 1:1 and 10:1.

The catalytic syntheses using the ligands (I) can be performed in either absence or presence of a solvent, wherein the solvent can have a positive influence on activity or enantioselectivity, or can facilitate the separation of the product and catalyst. As the solvent, typical organic solvents, such as benzene, toluene, methylene chloride, ethanol, methanol, tetrahydrofuran, diethyl ether, methyl, t-butyl ether or ionic liquids may be used. Water is also suitable as a solvent when the ligand is sufficiently soluble in water due to suitable polar substituents (e.g., COOH, $NH^{3+}$, $SO^{3-}$, see *Angew. Chem.*

1993, 105, 1588). The reactions may also be performed in supercritical carbon dioxide as the solvent if adequate solubility is ensured by suitable substituents (e.g., perfluoroalkyl residues, see PCT application WO 98/32533). To facilitate separation from the reaction products, the ligands (I) can be bound to solid supports using known methods (adsorption, inclusion, covalent bonding: *Synthesis* 1997, 1217). Product from catalyst separation can be achieved by running the reactions under biphasic conditions (e.g. see *Multiphase Homogeneous Catalysis*, Eds.: B. Cornils, W. A. Herrmann, D. Vogt, I. Horvath, H. Olivier-Bourbigon, W. Leitner, S. Mecking; Wiley-VCH, 2005) or by selectively extracting the products with an additional solvent after the reaction. The scope of application of ligands (I) includes asymmetric reductions (e.g., hydrogenation, transfer hydrogenation), asymmetric carbon-carbon bond formation (e.g., hydroformylation, Heck coupling, allylic alkylation, hydrocyanation, hydrovinylation, polymerization) and asymmetric bond formation between carbon and heteroatoms (e.g., hydroboration, hydrosilylation, hydroamination, hydrophosphination and hydrophosphorylation).

Enantioselective hydroformylation is an efficient method for the synthesis of chiral, non-racemic aldehydes from olefins (*Catalytic Asymmetric Synthesis*, Ed.: I. Ojima, VCH, Weinheim, 1993, pages 273ff). This type of reaction has met with great interest especially as a possible approach to chiral building blocks for the production of flavouring agents, cosmetics, plant protectants, food additives (vitamins) and pharmaceuticals (*Chirality* 1991, 3, 355). In particular, there may be mentioned the preparation of the anti-inflammatory and analgesic drugs ibuprofen and naproxen by oxidation of the corresponding aldehydes, which can be obtained from vinyl arenes by means of enantioselective hydroformylation. In addition to enantioselectivity, in this reaction, chemoselectivity (side reaction is predominantly hydrogenation) and regioselectivity in favour of the branched chiral aldehyde are of particular importance. Preferred catalysts for the hydroformylation are formed on the basis of the metals Fe, Co, Ir, Ru, Pt, Rh, more preferably on the basis of Pt and Rh. The molar ratio of ligand/metal should be between 1:1 and 10:1, preferably between 1:1 and 4:1. The molar ratio of substrate and catalyst can be widely varied, and preferably a ratio of between 100:1 and 10,000:1 may be used. The gases hydrogen and carbon monoxide can be added to the reactor either separately or as a mixture. The partial pressure of the individual gases is within a range of from 1 to 100 bar. The total pressure of synthesis gas can be within a range of from 1 to 200 bar, preferably within a range of from 10 to 100 bar. The reaction temperature can be widely varied and is between −20° C. and 150° C., preferably between 20° C. and 80° C.

Enantioselective hydrogenation is an efficient method for the synthesis of chiral, non-racemic organic compounds (*Catalytic Asymmetric Synthesis*, Ed.: I. Ojima, VCH, Weinheim, 1993, pages 1ff), which is of great importance, in particular, to the preparation of biologically active substances. Enantioselective hydrogenation is known for a wide variety of functional groups, especially for substrates with prochiral C=C, C=N or C=O double bonds. The hydrogenation of dehydroamino acids is an attractive approach to natural and non-natural amino acids and has already found a technical application, for example, in the preparation of L-Dopa, a medicament against Parkinson's disease (*Topics in Catalysis* 1998, 5, 3). Preferred catalysts for hydrogenation with ligands of the present invention are formed on the basis of the metals Pd, Pt, Co, Ir, Rh and Ru. The molar ratio of ligand/metal should be between 1:1 and 10:1, preferably between 1:1 and 2.5:1. The molar ratio of substrate and catalyst can be widely varied and is preferably between 100:1 and 100, 000:1. The partial pressure of hydrogen during hydrogenation should be within a range of from 0.3 to 200 bar, preferably between 10 and 100 bar. The reaction temperature can be widely varied and is between −20° C. and 150° C., preferably between 20° C. and 60° C.

In transfer hydrogenation a hydrogen donor such as isopropanol or formic acid may be used with catalysts of the type [(sulphonylated diamine) RuCl (arene)] for the reduction of carbonyl groups. Phosphorus compound-containing catalysts according to the present invention may also be used. This technology provides a powerful complement to catalytic asymmetric hydrogenation. Transfer hydrogenation, in fact, is particularly suitable for the asymmetric reduction of ketones that are difficult substrates for hydrogenation, such as acetylenic ketones and cyclic ketones.

Enantioselective hydroboration is a typical example of a reaction with formation of a carbon-heteroatom bond. It has met with great interest since the boranes produced are interesting intermediates for further syntheses (e.g., formation of chiral alcohols, carbon-carbon bond formation, etc.) (*Tetrahedron* 1997, 53, 4957). In addition to the enantioselectivity of the carbon-boron bond formation, chemoselectivity (side reaction is predominantly reduction) and regioselectivity are also important characteristics of this reaction. Preferred catalysts for the hydroboration with ligands (I) are formed on the basis of Rh. The molar ratio of ligand/metal should be between 1:1 and 4:1, preferably between 1:1 and 2:1. The molar ratio of substrate and catalyst can be widely varied and is preferably between 100:1 and 10,000:1. The reaction temperature can be widely varied and is between −80° C. and 100° C., preferably between 20° C. and 80° C.

The invention is further illustrated by reference to the following Examples.

Anhydrous solvents were purchased from Fluka and used as received in SureSeal™ bottles over molecular sieves. All reagents were purchased from commercial sources and used without further purification.

Example 1

Preparation of 8-Diphenylphosphino-2-methyl-1,2,3,4-tetrahydroquinoline (7)

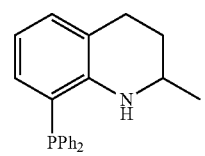

7

(a) synthesis of 8-Diphenylphoshinoquinoline (1)

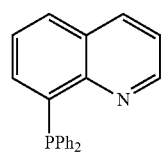

1

To a stirred solution of 8-bromoquinoline (20.8 g, 100 mmol) in dry THF (200 mL) under nitrogen was added n-BuLi (62.5 mL, 1.6 M in hexanes, 100 mmol) at −78° C. and the mixture was stirred for 30 minutes. Chlorodiphenylphosphine (17.9 mL, 100 mmol) was then added and the solution was allowed to warm up to room temperature and stirred for 2 h. The solution was then cooled to −78° C. and quenched by addition of saturated aqueous NH₄Cl solution (100 mL). After warming up to room temperature, the solution was filtered, the precipitated solid collected, taken up in CH₂Cl₂ (200 mL) and filtered over silica gel eluting with further portions of CH₂Cl₂ (4×200 mL). The combined filtrates were evaporated to give 1 as a light yellow solid (19 g, 60% yield). ¹H NMR (400.13 MHz, CDCl₃) δ 8.37 (dd, 1H, J=4.0, 1.6 Hz, C²—H), 8.17 (dd, 1H, J=8.0, 1.6 Hz, C³—H), 7.82 (d, 1H, J=8.4 Hz, C⁵—H), 7.44 (t, 1H, J=7.6 Hz, C⁶—H), 7.40 (dd, 1H, J=8.0, 4.0 Hz, C⁴—H), 7.3-7.2 (m, 10H, Ph-H), 7.14 (ddd, 1H, J=7.2, 3.6, 1.6 Hz, C¹'—H) ppm; ¹³C NMR (100.61 MHz, CDCl₃) δ 149.8, 149.6 (d, J=17.2 Hz), 138.4 (d, J=12.1 Hz), 137.4 (d, J=11.1 Hz), 136.2, 134.4, 134.2 (d, J=21.2 Hz), 128.8, 128.4 (d, J=19.2), 127.9, 126.57, 121.41 ppm; ³¹P NMR (161.97 MHz, CDCl₃) δ 15.0 ppm.

b) Synthesis
8-Diphenylphosphino-2-methyl-1,2-dihydroquinoline (2)

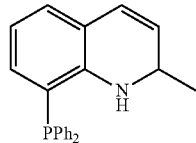

2

To a stirred solution of 8-diphenylphoshinoquinoline (1) (10 g, 31.95 mmol) in dry THF (150 mL) under nitrogen was added MeLi (39.9 mL, 1.6 M in diethyl ether, 1 mmol) at −78° C. and the solution was stirred at 0° C. for 10 minutes. The solution was cooled down to −78° C., saturated aqueous NH₄Cl solution (100 mL) was added and the mixture was warmed to room temperature. Products were extracted with EtOAc, washed with water and saturated aqueous NaCl, dried (MgSO₄) and evaporated to give 2 as a yellow oil, which solidified on standing (10.5 g, quantitative). ¹H NMR (400.13 MHz, CDCl₃) δ 7.4-7.25 (m, 10H, Ph-H), 6.86 (dd, 1H, J=7.2, 1.2, C⁵—H), 6.63 (ddd, 1H, J=7.6, 6.0, 1.6 Hz, C⁷—H), 6.49 (t, 1H, J=7.6 Hz, C⁶—H), 6.29 (d, 1H, J=9.6 Hz, C⁴—H), 5.54 (ddd, 1H, J=10.0, 4.0, 2.0 Hz, C³—H), 4.71 (d, 1H, J=7.6 Hz, N¹—H), 4.35 (m, 1H, C²—H), 1.15 (d, 3H, J=6.4 Hz, C¹'—CH₃) ppm; ¹³C NMR (100.61 MHz, CDCl₃) δ 147.0 (d, J=18.2 Hz), 135.5 (d, J=13.1 Hz), 135.4 (d, J=12.1 Hz), 134.2 (d, J=5.1 Hz), 133.4 (d, J=18.2 Hz), 133.3 (d, J=18.2 Hz), 128.5 (d, J=11.1 Hz), 128.4 (d, J=12.1 Hz), 128.0, 117.0, 116.1, 48.2, 24.2 ppm; ³¹P NMR (161.97 MHz, CDCl₃) δ −23.2 ppm.

c) Conversion of (2) to 8-Diphenylphosphinoyl-2-methyl-1,2-dihydroquinoline (5)

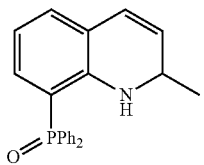

5

To a solution of 8-diphenylphosphino-2-methyl-1,2-dihydroquinoline (2) (10.5 g, 32 mmol) in CH₂Cl₂ (100 mL) was added H₂O₂ (6.6 mL, 30% w/w in H₂O, 63.9 mmol) at 0° C. and the solution was stirred at room temperature for 1 hour. The solution was then cooled to 0° C., saturated aqueous Na₂SO₃ solution (10 mL) was added and the mixture was warmed to room temperature. Products were extracted with EtOAc, washed with water and saturated aqueous NaCl, dried (MgSO₄) and evaporated to give 5 as a yellow oil (11 g, quantitative). ¹H NMR (400.13 MHz, CDCl₃) δ 7.7-7.6 (m, 4H, Ph-H), 7.6-7.5 (m, 2H, Ph-H), 7.5-7.4 (m, 4H, Ph-H), 6.97 (bs, 1H, N¹—H), 6.87 (d, 1H, J=7.2 Hz, C⁵—H), 6.55 (ddd, 1H, J=14.0, 8.0, 1.6 Hz, C⁷—H), 6.36 (ddd, 1H, J=10.0, 7.6, 2.8 Hz, C⁶—H), 6.22 (d, 1H, J=10.0 Hz, C⁴—H), 5.51 (ddd, 1H, J=10.0, 4.0, 2.0 Hz, C³—H), 4.43 (m, 1H, C²—H), 1.17 (d, 3H, J=6.8 Hz, C¹'—CH₃) ppm; ¹³C NMR (100.61 MHz, CDCl₃) δ 148.2 (d, J=5.1 Hz), 146.0 (d, J=6.1 Hz), 135.7 (d, J=8.1 Hz), 134.8, 132.4, 131.3 (d, J=5.1 Hz), 131.0 (d, J=11.1 Hz), 130.8 (d, J=10.1 Hz), 130.7 (d, J=10.1 Hz), 130.1, 129.2, 127.2 (d, J=12.1 Hz), 126.6 (d, J=13.1 Hz), 126.3, 125.0 (d, J=8.1 Hz), 124.1 (d, J=13.1 Hz), 122.8, 121.1, 119.7 (d, J=8.1 Hz), 113.6 (d, J=14.1 Hz), 107.3, 106.2, 46.9, 23.5 ppm; ³¹P NMR (161.97 MHz, CDCl₃) δ 36.0 ppm.

d) Conversion of (5) to 8-Diphenylphosphinoyl-2-methyl-1,2,3,4-tetrahydroquinoline (6)

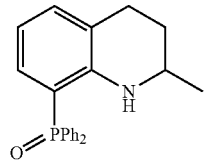

6

A suspension of 8-diphenylphosphinoyl-2-methyl-1,2-dihydroquinoline (5) (11 g, 32 mmol) and Pd/C (1.1 g, 10 wt %) in MeOH (40 mL) was stirred under H₂ at 145 psi pressure for 16 hours. The mixture was then diluted with EtOAc (200 mL) and filtered over celite (~25 mL). The filtrate was then evaporated to give compound 6 as a yellow oil (11.2 g, quantitative). ¹H NMR (400.13 MHz, CDCl₃) δ 7.7-7.6 (m, 4H, Ph-H), 7.6-7.5 (m, 2H, Ph-H), 7.5-7.4 (m, 4H, Ph-H), 7.03 (d, 1H, J=7.2 Hz, C⁵—H), 6.87 (bs, 1H, N¹—H), 6.58 (dd, 1H, J=14.0, 7.2 Hz, C⁷—H), 6.39 (ddd, 1H, J=10.4, 7.2, 2.8 Hz, C⁶—H), 3.5-3.4 (m, 1H, C²—H), 2.8-2.7 (m, 2H, C⁴—H), 1.9-1.8 (m, 1H, C³ᵃ—H), 1.6-1.4 (m, 1H, C³ᵇ—H), 1.13 (d, 3H, J=6.4 Hz, C¹'—CH₃) ppm; ¹³C NMR (100.61 MHz, CDCl₃) δ 148.9, 132.0 (d, J=11.1 Hz), 131.5, 131.0 (d, J=10.1 Hz), 130.7 (d, J=10.1 Hz), 130.6 (d, J=10.1 Hz), 130.4 (d, J=6.1 Hz), 130.3 (d, J=6.1H), 130.1 (d, J=11.1 Hz), 127.0 (d, J=13.1 Hz), 126.9 (d, J=12.1 Hz), 120.4 (d, J=8.1 Hz), 112.5 (d, J=14.1 Hz), 107.9, 106.9, 45.4, 27.4, 25.5, 20.9 ppm; ³¹P NMR (161.97 MHz, CDCl₃) δ 36.4 ppm.

e) Conversion of (6) to 8-Diphenylphosphino-2-methyl-1,2,3,4-tetrahydroquinoline (7)

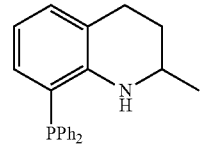

7

To a solution of 8-diphenylphosphinoyl-2-methyl-1,2,3,4-tetrahydroquinoline (6) (1.5 g, 4.5 mmol) in dry degassed toluene (40 mL) was added degassed Et₃N (3.15 mL, 22.5 mmol) followed by trichlorosilane (2.25 mL, 22.5 mmol).

The mixture was stirred at 80° C. for 30 minutes before cautiously adding 2N NaOH (150 mL) and cooling down to room temperature. Products were then extracted with EtOAc, washed with water and saturated aqueous NaCl, dried (MgSO$_4$) and evaporated to give a yellow oil. This oil was taken up in CH$_2$Cl$_2$ (100 mL), and filtered over silica gel (~25 mL) eluting with further portions of CH$_2$Cl$_2$ (4×100 mL). The combined filtrates were then evaporated to give compound 7 (1.2 g) as a light yellow oil in 80% yield. $^1$H NMR (400.13 MHz, CDCl$_3$) δ 7.4-7.3 (m, 10H, Ph-H), 6.99 (d, 1H, J=7.2 Hz, C$^5$—H), 6.62 (ddd, 1H, J=7.2, 6.0, 1.2 Hz, C$^7$—H), 6.52 (t, 1H, J=7.6 Hz, C$^6$—H), 4.65 (bs, 1H, N$^1$—H), 3.4-3.3 (m, 1H, C$^2$—H), 2.9-2.7 (m, 2H, C$^{4a/b}$—H), 2.0-1.9 (m, 1H, C$^{3a}$—H), 1.6-1.5 (m, 1H, C$^{3b}$—H), 1.11 (d, 3H, J=6.4 Hz, C$^{1'}$—CH$_3$) ppm; $^{13}$C NMR (100.61 MHz, CDCl$_3$) δ 147.9 (d, J=18.2 Hz), 147.7 (d, J=18.2 Hz), 136.1 (d, J=12.1 Hz), 136.0 (d, J=13.1 Hz), 135.8 (d, J=13.1 Hz), 135.7 (d, J=13.1 Hz), 134.1-133.5 (m), 132.5 (d, J=12.1 Hz), 132.4 (d, J=12.1 Hz), 130.5 (d, J=13.1 Hz), 128.7-128.4 (m), 120.7 (d, J=12.1 Hz), 117.0, (d, J=12.1 Hz), 116.3 (d, J=12.1 Hz), 47.4, 39.6, 26.8, 22.4 ppm; $^{31}$P NMR (161.97 MHz, CDCl$_3$) δ −21.9 ppm.

The tetrahydroquinoline product 7 may be converted into a compound of formula (I) by reaction with a suitable oxychlorophosphite using e.g. the method in Example 4(b).

Example 2

Preparation of 8-Diphenylphosphino-2-phenyl-1,2,3,4-tetrahydroquinoline (3)

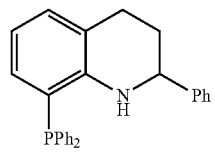

3 a) Synthesis of 8-Diphenylphosphino-2-phenyl-1,2-dihydroquinoline (4)

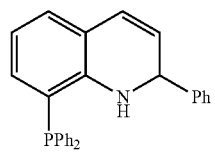

4

PhLi (0.56 mL, 1.8M in di-n-butyl ether, 1 mmol) was added to a stirred solution of 8-diphenylphoshinoquinoline (1) (156 mg, 0.5 mmol) in dry THF (5 mL) at −78° C. and the solution was stirred at 0° C. for 10 minutes. The solution was then cooled to −78° C., saturated aqueous NH$_4$Cl solution (10 mL) was added and the mixture was warmed to room temperature. Products were extracted with EtOAc, washed with water and saturated aqueous NaCl, dried (MgSO$_4$) and evaporated to give 4 (196 mg) quantitatively as a yellow oil. $^1$H NMR (400.13 MHz, CDCl$_3$) δ 7.4-7.3 (m, 15H, Ph-H), 6.92 (d, 1H, J=7.2 Hz, C$^5$—H), 6.69 (ddd, 1H, J=7.2, 6.0, 1.2 Hz, C$^7$—H), 6.54 (t, 1H, J=7.2 Hz, C$^6$—H), 6.38 (d, 1H, J=9.6 Hz, C$^4$—H), 5.64 (dd, 1H, J=10.0, 4.0 Hz, C$^3$—H), 5.44 (bs, 1H, N$^1$—H), 5.15 (d, 1H, J=7.2 Hz, C$^2$—H) ppm; $^{13}$C NMR (100.61 MHz, CDCl$_3$) δ 146.5 (d, J=19.2 Hz), 145.1, 135.4 (d, J=8.1 Hz), 135.3 (d, J=7.1 Hz), 134.5, 133.7 (d, J=18.2 Hz), 133.6 (d, J=19.2 Hz), 133.4 (d, J=19.2 Hz), 127.3, 128.7-128.3 (m), 127.1, 126.0, 125.2, 124.5, 119.1, 117.1, 116.1 (d, J=8.1 Hz), 57.6 ppm; $^{31}$P NMR (161.97 MHz, CDCl$_3$) δ −23.8 ppm.

b) Conversion of (4) to 8-Diphenylphosphinoyl-2-phenyl-1,2-dihydroquinoline (8)

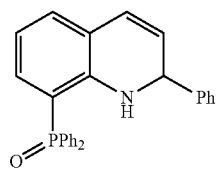

8

Following the procedure described for the synthesis of compound 5,8-diphenylphosphino-2-methyl-1,2-dihydroquinoline (4) (1.17 g, 3 mmol) was transformed into 8 (1.2 g) in 98% yield. $^1$H NMR (400.13 MHz, CDCl$_3$) δ7.8-7.5 (m, 15H, Ph-H), 7.48 (bs, 1H, N$^1$—H), 7.03 (d, 1H, J=7.2 Hz, C$^5$—H), 6.72 (ddd, 1H, J=9.2, 7.6, 1.2 Hz, C$^7$—H), 6.51 (td, 1H, J=7.6, 2.8 Hz, C$^6$—H), 6.40 (dt, 1H, J=10.0, 1.6 Hz, C$^4$—H), 5.73 (ddd, 1H, J=10.0, 4.4, 2.0 Hz, C$^3$—H), 5.60 (dd, 1H, J=3.6, 1.6 Hz, C$^2$—H) ppm; $^{13}$C NMR (100.61 MHz, CDCl$_3$) δ 148.2, 144.4, 132.0 (d, J=19.2 Hz), 131.9 (d, J=11.1 Hz), 131.2 (d, J=10.1 Hz), 131.1 (d, J=10.1 Hz), 131.0, 130.9, 129.7, 127.8, 127.6 (d, J=12.1 Hz), 127.5 (d, J=12.1 Hz), 126.2, 124.9, 124.7, 122.8, 119.1 (d, J=8.1 Hz), 114.0 (d, J=14.1 Hz), 108.3, 107.3, 56.0 ppm; $^{31}$P NMR (161.97 MHz, CDCl$_3$) δ 34.9 ppm.

c) Conversion of (8) into 8-Diphenylphosphinoyl-2-phenyl-quinoline (9)

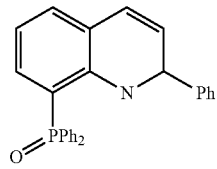

9

To a stirred solution of 8-diphenylphosphinoyl-2-phenyl-1,2-dihydroquinoline (8) (1.2 g, 2.95 mmol) in EtOAc (40 mL) was added Pd/C (1.2 g, 100 wt %) and the suspension was stirred overnight at room temperature. The mixture was then filtered over celite and evaporated to give 9 (1.19 g) quantitatively as a white solid. $^1$H NMR (400.13 MHz, CDCl$_3$) δ 8.63 (dd, 1H, J=14.0, 7.2 Hz, C$^7$—H), 8.16 (dd, 1H, J=8.8, 1.2 Hz, C$^5$—H), 7.86 (1H, d, J=8.4 Hz, C$^3$—H), 7.91 (dd, 4H, J=12.4, 7.2 Hz, Ph-H), 7.81 (dd, 1H, J=8.4 Hz, C$^4$—H), 7.65 (td, 1H, J=8.0, 2.0 Hz, C$^6$—H), 7.5-7.2 (m, 11H, Ph-H) ppm; $^{13}$C NMR (100.61 MHz, CDCl$_3$) δ 156.2, 147.4 (d, J=6.1 Hz), 138.4, 137.7 (d, J=7.1 Hz), 136.8, 134.3, 133.2, 132.2, 132.1, 131.9, 131.0, 129.3, 128.3, 128.0, 127.8, 127.4, 125.9, 125.7, 118.7 ppm; $^{31}$P NMR (161.97 MHz, CDCl$_3$) δ 27.7 ppm.

d) Conversion of (9) into 8-Diphenylphosphinoyl-2-phenyl-1,2,3,4-tetrahydroquinoline (10)

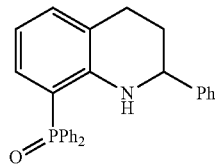

10

Following the procedure previously described for the synthesis of compound 6,8-diphenylphosphinoyl-2-phenyl-quinoline (9) (50 mg, 0.12 mmol) was quantitatively transformed into compound 10 (51 mg). $^1$H NMR (400.13 MHz, CDCl$_3$) δ 7.8-7.4 (m, 10H, Ph-H), 7.09 (bs, 1H, N—H), 7.08 (1H, d, J=7.6 Hz, C$^5$—H), 7.2-7.0 (3H, m, Ph-H), 7.0-6.9 (m, 2H, Ph-H), 6.66 (ddd, 1H, J=14.4, 7.6, 1.2 Hz, C$^7$—H), 6.47 (td, 1H, J=7.6, 3.2 Hz, C$^6$—H), 4.57 (m, 1H, C$^2$—H), 2.84 (m, 1H, C$^{4a}$—H), 2.63 (m, 1H, C$^{4b}$—H), 2.09 (m, 1H, C$^{3a}$—H), 1.84 (m, 1H, C$^{3b}$—H) ppm; $^{13}$C NMR (100.61 MHz, CDCl$_3$) δ 149.4 (d, J=4.1 Hz), 144.5, 133.1, 132.8, 132.2-131.3 (m), 128.4, 128.2, 128.1, 126.7, 125.8, 121.8 (d, J=15.2 Hz), 114.3 (d, J=16.2 Hz), 109.8, 55.2, 29.7, 26.1 ppm; $^{31}$P NMR (161.97 MHz, CDCl$_3$) δ 35.5 ppm; HPLC (DAICEL-CHIRAPAK-AD, Hexane:IPA 60:40, 1 mL/min, 25° C., 210 nm) τ$_1$=6.34, τ$_2$=8.91.

e) Conversion of (10) to 8-Diphenylphosphino-2-phenyl-1,2,3,4-tetrahydroquinoline (3)

The product phosphine may be produced by treating compound (10) according to the method described for the conversion of compound (6) into compound (7).

The tetrahydroquinoline phosphine product may be converted into a compound of formula (I) by reaction with a suitable oxychlorophosphite using e.g. the method in Example 4(b).

Example 3

Preparation of 8-Diphenylphosphino-2-naphthalen-1-yl-1,2,3,4-tetrahydroquinoline (14)

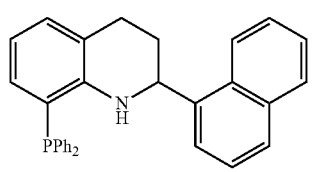

14 a) Synthesis of 8-Diphenylphosphino-2-naphthalen-1-yl-1,2-dihydroquinoline (11)

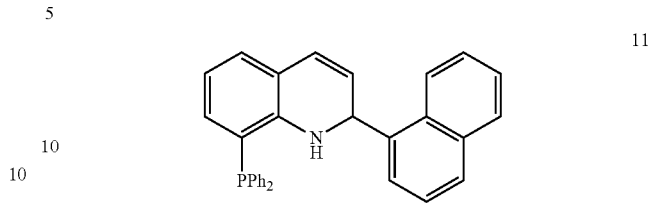

11

To a solution of 1-bromonaphthalene (8.57 mL, 60 mmol) in dry THF (100 mL) under nitrogen was added n-BuLi (37.5 mL, 1.6 M in hexanes, 60 mmol) at −78° C. and the solution was stirred for 30 minutes at −78° C. before adding 8-diphenylphoshinoquinoline (1) (9.4 g, 30 mmol). After stirring at 0° C. for 10 minutes the solution was again cooled down to −78° C., saturated aqueous NH$_4$Cl solution (10 mL) was added and the mixture was warmed to room temperature. Products were then extracted with EtOAc, washed with water and saturated aqueous NaCl, dried (MgSO$_4$) and evaporated to give the 11 as a tan solid (13.0 g, 98%). $^1$H NMR (400.13 MHz, CDCl$_3$) δ 8.0-7.9 (m, 1H, C$^{5'}$—H), 7.8-7.7 (m, 1H, C$^{8'}$—H), 7.66 (d, 1H, J=8.0 Hz, C$^{2'}$—H), 7.5-7.3 (m, 2H, C$^{6'/7'}$—H), 7.36 (d, 1H, J=6.4 Hz, C$^{4'}$—H), 7.3-7.1 (m, 11H, C$^{3'}$—H/Ph-H), 6.86 (dd, 1H, J=7.2, 1.2 Hz, C$^5$—H), 6.64 (ddd, 1H, J=8.0, 6.4, 1.6 Hz, C$^7$—H), 6.48 (t, 1H, J=7.6 Hz, C$^6$—H), 6.35 (dd, 1H, J=9.6, 1.6 Hz, C$^4$—H), 6.16 (t, 1H, J=1.6 Hz, C$^2$—H), 5.70 (ddd, 1H, J=10.0, 3.6, 1.6 Hz, C$^3$—H), 5.02 (bd, 1H, J=7.6 Hz, N—H) ppm; $^{13}$C NMR (100.61 MHz, CDCl$_3$) δ 146.6, 146.5, 139.8, 129.5, 128.7, 128.6, 128.5, 128.4, 128.3 (m), 127.7, 135.1 (d, J=8.1 Hz), 134.9 (d, J=7.1 Hz), 134.5 (d, J=5.1 Hz), 133.9, 133.5 (d, J=13.1 Hz), 133.3 (d, J=12.1 Hz), 126.2, 125.6, 125.3, 125.2, 124.8, 124.4, 122.5, 118.8, 117.1, 116.3, 54.0 ppm; $^{31}$P NMR (161.97 MHz, CDCl$_3$) δ −23.1 ppm.

b) Conversion of (11) into 8-Diphenylphosphinoyl-2-naphthalen-1-yl-1,2-dihydroquinoline (12)

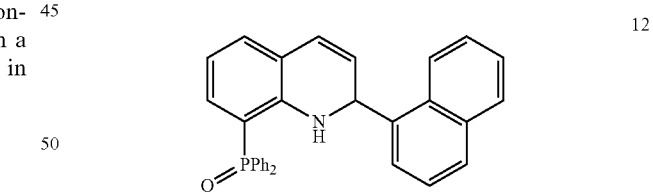

12

Following the procedure described for the synthesis of compound 5,8-diphenylphosphino-2-naphthale-1-yl-1,2-dihydroquinoline (11) (8.8 g, 20 mmol) in CH$_2$Cl$_2$ (60 mL) was oxidised with H$_2$O$_2$ (4.15 mL, 30% w/w in H$_2$O, 40 mmol) to give compound 12 (8.3 g) in 91% yield. $^1$H NMR (400.13 MHz, CDCl$_3$) δ 8.00 (d, 1H, J=8.4 Hz, C$^{5'}$—H), 7.83 (dd, 1H, J=7.6, 2.0 Hz, C$^{8'}$—H), 7.7-7.6 (m, 3H, C$^{2'}$—H/Ph-H), 7.6-7.5 (m, 3H, Ph-H), 7.5-7.4 (m, 5H, C$^{6'/7'}$—H/Ph-H), 7.4-7.3 (m, 2H, Ph-H), 7.29 (d, 1H, J=8.0 Hz, C$^{4'}$—H), 7.19 (t, 1H, J=8.0 Hz, C$^{3'}$—H), 6.96 (d, 1H, J=7.2 Hz, C$^5$—H), 6.64 (ddd, 1H, J=13.6, 7.6, 1.2 Hz, C$^7$—H), 6.44 (td, 1H, J=7.2, 2.8 Hz, C$^6$—H), 6.34 (dt, 1H, J=10.0, 1.6 Hz, C$^4$—H), 6.32 (t, 1H, J=1.6 Hz, C$^2$—H), 5.78 (dd, 1H, J=10.0, 4.0 Hz, C$^3$—H) ppm; $^{13}$C NMR (100.61 MHz, CDCl$_3$) δ 148.3, 148.2, 139.2, 132.9, 131.9 (d, J=11.1 Hz), 131.8 (d, J=12.1 Hz), 131.2 (d, J=10.1 Hz), 130.9 (d, J=9.1 Hz), 130.7, 129.8, 128.4, 127.8, 127.5 (d, J=12.1), 127.3 (d J=12.1), 126.6, 125.3, 124.7, 124.5, 123.8, 123.7, 123.4, 121.5, 121.5, 118.9, 114.2, 114.0, 108.9, 107.8, 52.6 ppm; $^{31}$P NMR (161.97 MHz, CDCl$_3$) δ+35.2 ppm.

c) Conversion of (12) into 8-Diphenylphosphinoyl-2-naphthalen-1-yl-1,2,3,4-tetrahydroquinoline

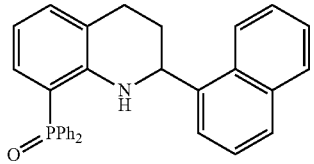

13

Following the procedure previously described for the synthesis of compound 6,8-diphenylphosphinoyl-2-naphthalen-1-yl-1,2-dihydroquinoline (12) (8.3 g, 18.2 mmol) was quantitatively transformed into compound 13 (8.3 g). $^1$H NMR (400.13 MHz, CDCl$_3$) δ 8.0-9.9 (m, 1H, C$^{5'}$—H), 7.9-7.8 (m, 1H, C$^{8'}$—H), 7.8-7.6 (m, 5H, C$^{3'}$/C$^{6'/7'}$—H/Ph-H), 7.7-7.4 (m, 8H, Ph-H), 7.23 (bs, 1H, N—H), 7.18 (t, 1H, J=7.6 Hz, C$^5$—H), 7.12 (d, 1H, J=7.2 Hz, C$^{2'}$—H), 7.06 (d, 1H, J=7.2 Hz, C$^{4'}$—H), 6.71 (ddd, 1H, J=14.4, 8.0, 1.2 Hz, C$^7$—H), 6.51 (td, 1H, J=7.2, 2.4 Hz, C$^6$—H), 6.41 (t, 1H, J=1.6 HZ, C$^2$—H), 2.9-2.8 (m, 1H, C$^{4a}$—H), 2.7-2.6 (m, 1H, C$^{4b}$—H), 2.3-2.2 (m, 1H, C$^{3a}$—H), 2.0-1.9 (m, 1H, C$^{3b}$—H) ppm; $^{13}$C NMR (100.61 MHz, CDCl$_3$) δ 149.8, 149.7, 139.6, 133.7, 133.3, 132.9, 132.8, 132.1 (d, J=10.1 Hz), 131.8 (d, J=8.0 Hz), 131.7 (d, J=7.1 Hz), 131.5 (d, J=12.1 Hz), 130.0, 128.8, 128.3 (d, J=12.1 Hz), 127.2, 125.8, 125.4, 125.2, 123.40, 122.4, 121.6 (d, J=8.1 Hz), 133.4, 133.3, 110.9, 109.9, 51.5, 27.8, 25.9 ppm; $^{31}$P NMR (161.97 MHz, CDCl$_3$) δ +34.6 ppm; HPLC (DAICEL-CHIRAPAK-AD, Hexane:IPA 60:40, 1 mL/min, 25° C., 210 nm) τ$_1$=7.23, τ$_2$=14.6.

d) Conversion of (13) into 8-Diphenylphosphino-2-naphthalen-1-yl-1,2,3,4-tetrahydroquinoline (14)

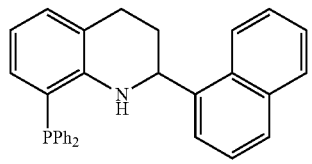

14

Following the procedure described for compound 7,8-diphenylphosphinoyl-2-naphthalen-1-yl-1,2,3,4-tetrahydroquinoline (13) (8.3 g, 18.1 mmol) was reduced to give compound 14 (5.0 g) as a white solid in 62% yield. $^1$H NMR (400.13 MHz, CDCl$_3$) δ 7.89 (d, 1H, J=8.0 Hz, C$^5$—H), 7.73 (d, 1H, J=7.6 Hz, C$^{8'}$—H), 7.61 (d, 1H, J=8.0 Hz, C$^{2'}$—H), 7.4-7.2 (m, 12H, C$^{6'/7'}$—H/Ph-H), 7.17 (t, 1H, J=7.6 Hz, C$^{3'}$—H), 7.12 (d, 1H, J=6.0 Hz, C$^{4'}$—H), 6.94 (d, 1H, J=7.2 Hz, C$^5$—H), 6.61 (td, 1H, J=7.2, 1.6 Hz, C$^7$—H), 6.50 (t, 1H, J=7.2 Hz, C$^6$—H), 5.21 (dd, 1H, J=6.8, 2.4 Hz, C$^2$—H), 4.99 (d, 1H, J=7.2 Hz, N—H), 2.9-2.8 (m, 1H, C$^{4a}$—H), 2.62 (m, 1H, C$^{4b}$—H), 2.3-2.1 (m, 1H, C$^{3a}$—H), 2.0-1.9 (m, 1H, C$^{3b}$—H) ppm; $^{13}$C NMR (100.61 MHz, CDCl$_3$) δ 147.4, 147.2, 139.7, 135.5 (d, J=12.1 Hz), 135.4 (d, J=11.1 Hz), 133.9, 133.8, 133.6 (d, J=13.1 Hz), 132.2, 130.2 (d, J=15.1 Hz), 128.8 (d, J=11.1 Hz), 128.6, 128.5, 128.4, 127.4, 125.9, 125.4 (d, J=13.1 Hz), 123.3, 122.5, 120.3, 117.6, 116.4, 52.2, 28.7, 26.3 ppm; $^{31}$P NMR (161.97 MHz, CDCl$_3$) δ −21.3 ppm.

Example 4

Preparation of (R$_a$,S$_c$)-3,4-dihydro-(1-naphthyl)-QUINAPHOS 17

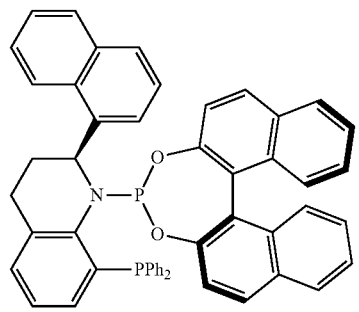

a) Synthesis of (R)- and (S)-2,2'binaphthyl-1,1'-oxy-chlorophosphite

A suspension of (R)- or (S)-2,2'-binaphthyl (8.6 g, 30 mmol) and 1-methyl-2-pyrrolidone (0.001 g, 0.01 mmol) in PCl$_3$ (26 mL, 300 mmol) was warmed to 75° C. and then stirred for 5 mins. Excess PCl$_3$ was removed under reduced pressure and then final traces removed by azeotropic distillation with toluene (3×10 mL) in vacuo. Products obtained as white solids and were taken forward as solutions in toluene.

b) Conversion of (14) to (R$_a$,S$_c$)-3,4-dihydro-(1-naphthyl)-QUINAPHOS 17

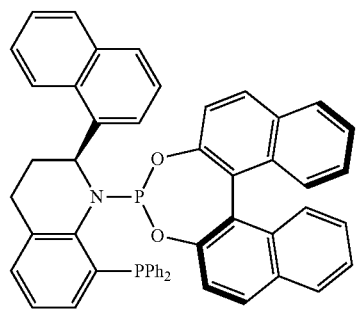

To a solution of 8-diphenylphosphino-2-(1-naphthyl)-1,2,3,4-tetrahydro-quinoline 14 (1.858 mmol, 824 mg) in dry THF (20 mL) under Ar, phenyllithium (1 eq, c=1.84 mol/L in di-n-butylether/Cyclohexane, 1.01 mL) was added at −20° C. and the resulting solution was stirred for 1 h at the same temperature. (R)-1,1'-binaphthyl-2,2'-dioxychlorophosphite (1 eq, c=0.5 mol/L in toluene, 3.72 mL) was then added and the resulting mixture was slowly allowed to warm to RT and stirred for an additional hour. After removal of the volatiles under vacuum, the residue was re-crystallised from dry toluene (18 mL) adding dry ethanol (24 mL). After removal of the mother liquor the title compound was obtained as a white solid (696.7 mg) with a diastereomeric purity of 95:5 $R_a,S_c$: $R_a,R_c$. A second re-crystallisation from toluene (19 mL) ethanol (15 mL) yielded diastereomerically pure ($R_a,S_c$)-17 (368.8 mg, 26%). $^1$H NMR (600.07 MHz, CDCl$_3$, 296 K) δ 8.25 (d, J=8.7 Hz, 1H), 8.15 (d, J=8.0 Hz, 1H), 7.83 (d, J=8.7 Hz, 2H), 7.79 (d, J=8.7 Hz, 1H), 7.60-7.52 (m, 4H), 7.49-7.35 (m, 9H), 7.35-7.25 (m, 9H), 7.16-7.10 (m, 1H), 7.06-6.98 (m, 2H), 6.16 (d, J=8.6 Hz, 1H), 6.11 (t, J=7.6 Hz, 1H), 5.65 (t, J=8.3 Hz, 1H), 3.20-3.09 (m, 1H), 2.82-2.73 (m, 1H), 2.68-2.59 (m, 1H), 1.66-1.55 (m, 1H) ppm. $^{31}$P NMR (242.91 MHz, CDCl$_3$, 296 K) δ 138.2 (d, J=184.9 Hz, P(O)$_2$N), −19.9 (d, J=184.9 Hz, PPh$_2$) ppm.

Example 5

Synthesis of [Rh(cod)(PP*)][BF$_4$], PP*=($R_a,S_c$)-3,4-Dihydro-(1-Nph)-QUINAPHOS 18

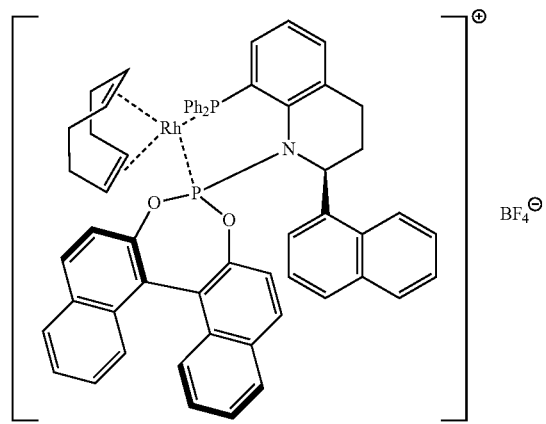

To a stirred solution of (2,4-acetylacetonato)-1,5-cyclooctadien-rhodium(I) (149.2 µmol, 46.3 mg) in dry THF (6 mL) under Ar, HBF$_4$.Et$_2$O (179 µmol, 25 µL, 1.2 eq) was added. After stirring for 10 min, a solution of ($R_a,S_c$)-17 (149.2 µmol) in THF (7 mL) was added dropwise. The mixture was stirred for 30 min and the solution was concentrated under vacuum (ca. 5 mL). By adding dry pentane (15 mL) a yellow solid precipitated which was collected and dried under vacuum (148.8 mg). This solid was re-crystallised from CH$_2$Cl$_2$ (5 mL)/diethylether (25 mL) in order to remove occluded THF molecules. The title compound was obtained as a yellow solid (94.3 mg, 60%). $^{31}$P NMR (121.28 MHz, CDCl$_3$, 300 K) δ 137.8 (dd, J=251.0 Hz, J=68.2 Hz, P(O)$_2$N), 23.5 (dd, J=136.6 Hz, J=68.2 Hz, PPh$_2$) ppm.

Example 6

Asymmetric Hydrogenation with 18

In a Ar-flushed stainless steel autoclave 1 mL of a stock solution of the substrate (1 M, 1 mmol) and 1 mL of a stock solution of [Rh(cod)(18)][BF$_4$] (1 mM, 1 µmol) in CH$_2$Cl$_2$ were introduced. The autoclave was pressurised with H$_2$ (30 bar) and the stirrer was switched on. After the reaction time given in the table, the autoclave was vented and the reaction mixture analyzed by GC. The results were as follows;

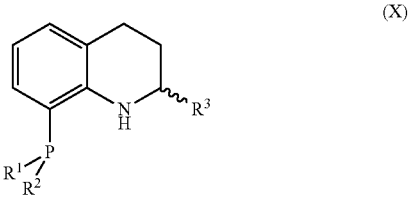

| | | |
|---|---|---|
| conv. [%] | >99 | >99 |
| t [min] | 5 | 3 |
| Sub/Rh | 1000 | 1000 |
| ee [%] | >99 (S) | >99 (R) |
| TOF [h$^{-1}$] | >12000 | >15000 |

The invention claimed is:

1. A chiral phosphorus compound of formula (X):

(X)

wherein R$^1$, R$^2$, R$^3$ are chiral or achiral groups selected from the list consisting of substituted or unsubstituted straight-chain, branched-chain or cyclic aliphatic or aromatic groups and in which the pair R$^1$/R$^2$ may be interconnected to form a ring.

2. The chiral phosphorus compound according to claim 1, wherein R$^1$, R$^2$, R$^3$ are chiral or achiral groups selected from the list consisting of methyl, ethyl, n-propyl, i-propyl, n-butyl, t-butyl, hexyl, F(CF$_2$)$_m$(CH$_2$)$_n$ where m=1-10 and, n=0-4, cyclohexyl, menthyl, allyl, benzyl, —CH$_2$O(CH$_2$)$_2$OCH$_3$, phenyl, tolyl, anisyl, trifluoromethylphenyl, F(CF$_2$)$_m$(CH$_2$)$_n$ C$_6$H$_4$-where m=1-10 and n=0-4, bis(tri-fluoromethyl)phenyl, chlorophenyl, pentafluorophenyl, hydroxyphenyl, carboxyphenyl, NaO$_3$SC$_6$H$_4$—, naphthyl, fluorenyl, pyridyl and furyl.

3. The chiral phosphorus compound according to claim 1, wherein R$^1$ and R$^2$ are interconnected to form substituted or unsubstituted chiral or achiral bridges which are derived from the skeletons —(CH$_2$)$_n$— where n=2-4, —CH(CH$_3$)CH (CH$_3$)—, —CH(CH$_3$)CH$_2$CH(CH$_3$)—, 1,1'—bipheny-2,2'-diyl or 1,1'-binaphth-2,2'-diyl.

4. The chiral phosphorus compound according to claim 1, having the following structure

7

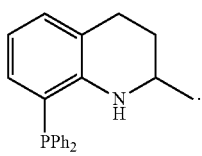

5. The chiral phosphorus compound according to claim 1, having the following structure

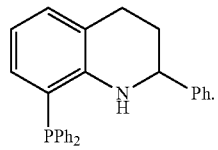

6. The chiral phosphorus compound according to claim 1, having the following structure

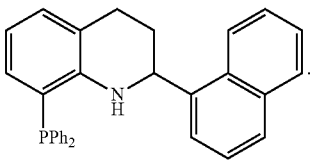

7. The chiral phosphorus compound according to claim 1, wherein the compound is enantiomerically enriched in the stereoisomer according to formula (Xa)

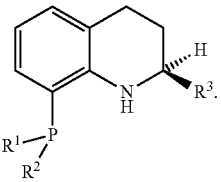
(Xa)

8. The chiral phosphorus compound according to claim 1, wherein the compound is enantiomerically enriched in the stereoisomer according to formula (Xb)

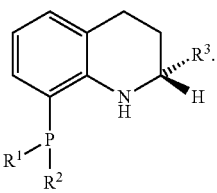
(Xb)

* * * * *